US007919465B2

(12) United States Patent
Gyongyossy-Issa et al.

(10) Patent No.: US 7,919,465 B2
(45) Date of Patent: Apr. 5, 2011

(54) PEPTIDE MIMOTOPES THAT INHIBITS INTERACTION BETWEEN A PLATELET RECEPTOR AND A PLATELET RECEPTOR LIGAND

(75) Inventors: Maria I. C. Gyongyossy-Issa, Vancouver (CA); Dana V. Devine, Vancouver (CA); Iren Constantinescu, Vancouver (CA); William Campbell, Surrey (CA); Carlos A. Del Carpio Munoz, Katahira (JP)

(73) Assignees: Maria I. C. Gyongyossy-Issa, Vancouver, BC (CA); Dana V. Devine, Vancouver, BC (CA); Iren Constantinescu, Vancouver, BC (CA); William Campbell, Richmond, BC (CA); Carlos A. Del Carpio Mundoz, Sendai (JP)

( * ) Notice: Subject to any disclaimer, the term of this patent is extended or adjusted under 35 U.S.C. 154(b) by 0 days.

(21) Appl. No.: 12/546,811

(22) Filed: Aug. 25, 2009

(65) Prior Publication Data

US 2010/0075908 A1 Mar. 25, 2010

Related U.S. Application Data

(63) Continuation-in-part of application No. 11/484,364, filed on Jul. 11, 2006, now abandoned.

(51) Int. Cl.
*A61K 38/10* (2006.01)
(52) U.S. Cl. .......................................... 514/14; 530/326
(58) Field of Classification Search ........................ None
See application file for complete search history.

(56) References Cited

U.S. PATENT DOCUMENTS

| | | | |
|---|---|---|---|
| 4,550,163 A | 10/1985 | Voss et al. | |
| 4,833,092 A * | 5/1989 | Geysen | 436/501 |
| 5,114,842 A | 5/1992 | Plow et al. | |
| 5,238,919 A | 8/1993 | Zimmerman et al. | |
| 5,321,127 A | 6/1994 | Handin | |
| 5,328,840 A | 7/1994 | Coller | |
| 5,336,667 A | 8/1994 | Kirby et al. | |
| 5,428,008 A | 6/1995 | Chao et al. | |
| 5,578,565 A | 11/1996 | Chao et al. | |
| 5,679,542 A | 10/1997 | Scarborough | |
| 5,817,748 A | 10/1998 | Miller et al. | |
| 5,844,098 A | 12/1998 | Chao et al. | |
| 5,877,155 A | 3/1999 | Miller et al. | |
| 5,977,313 A | 11/1999 | Heath et al. | |
| 6,008,193 A | 12/1999 | Garfinkel et al. | |
| 6,139,832 A | 10/2000 | Li et al. | |
| 6,177,059 B1 | 1/2001 | Matsuda et al. | |
| 6,264,988 B1 | 7/2001 | Yen | |
| 6,667,032 B2 | 12/2003 | Ni et al. | |
| 6,706,862 B1 | 3/2004 | Hornik | |
| 6,747,135 B1 | 6/2004 | Nolan et al. | |
| 6,825,319 B1 | 11/2004 | Blank et al. | |
| 6,858,210 B1 | 2/2005 | Marquis et al. | |
| 6,926,884 B2 | 8/2005 | Ikeda et al. | |
| 6,964,769 B2 | 11/2005 | Sebbel et al. | |

FOREIGN PATENT DOCUMENTS

| | | |
|---|---|---|
| EP | 0255206 | 2/1988 |
| WO | WO 93/11778 A1 | 6/1993 |
| WO | WO 93/16709 A1 | 9/1993 |
| WO | WO 95/01375 A1 | 1/1995 |
| WO | WO 00/56885 A1 | 9/2000 |
| WO | WO 01/10911 A2 | 2/2001 |
| WO | WO 02/063003 A2 | 8/2002 |
| WO | WO 2004/062551 A2 | 7/2004 |

OTHER PUBLICATIONS

Wrighton et al., 1996, Small peptides as potent mimetics of the protein hormone erythropoietin, Science, 273: 458-464.
Del Caprio et al., 2002, Proteins: structure, function and genetics, 48: 696-732.
Brasseur, 1991, J Biol Chem, 266: 16120-16127.
Kohonen, 1990, Proceedings IEEE, 78: 1464-1480.
Del Caprio, 1996, Journal of Chemical Information and Computer Sciences, 36: 258-269.
Ponder and Case, 2003, Advances in Protein Chemistry, 66: 27-85.
Shimizu et al., 2004, J Biol Chem, 279: 16285-16294.
Hauert et al., 2004, ChemBioChem, 8: 856-864.
Xu et al., 1997, Protein Engineering, 10: 999-1012.
Cauwenberghs et al., 2000, Antithrombotic effect of platelet glycoprotein Ib-blocking monoclonal antibody Fab fragments in nonhuman primates, Arterioscler Thromb Vasc Biol, 20: 1347-1353.
Kageyama et al., 2000, Anti-human von Willebrand factor monoclonal antibody AJvW-2 prevents thrombus deposition and neointima formation after balloon injury in guinea pigs, Arterioscler Thromb Vasc Biol, 20: 2303-2308.
Staelens et al., 2006, Paratope determination of the antithrombotic antibody 82D6A3 based on the crystal structure of its complex with the von Willebrand factor A3-domain, J Biol Chem, 281: 2225-2231.
Yeh et al., 2001, Pharmacological characterization and antithrombotic effect of agkistin, a platelet glycoprotein Ib antagonist, J Pharmacol, 132: 843-850.
del Carpio Munoz et al., 2008, Rational design of antithrombotic peptides to target the von Willebrand Factor (vWf)-GPIb integrin interaction, J Mol Model, DOI 10.1007/s00894-008-0375-z.
Miller et al., 1996, Mimotope/Anti-mimotope probing of structural relationships in platelet glycoprotein Ibalpha, PNAS, 93: 3565-3569.

* cited by examiner

*Primary Examiner* — Ruixiang Li
(74) *Attorney, Agent, or Firm* — Ogilvy Renault LLP

(57) ABSTRACT

It is provided mimotope receptors and inhibitors that employ peptide mimics that mimic the shape and function of natural receptors and ligands, thus providing synthetic binding sites for ligands and receptors. Receptor mimics can be attached to carriers, such as liposomes, to act as synthetic platelets, for example, by providing multiple binding sites for binding to other (natural or synthetic) platelets or to the endothelium. Synthetic platelets would have virtually limitless shelf life and would not require disease screening prior to transfusion, thereby providing a solution to the perpetual platelet shortages, as well as the safety and storage issues associated with natural blood platelets.

11 Claims, 12 Drawing Sheets

PEPTIDE MIMOTOPES THAT INHIBITS INTERACTION BETWEEN A PLATELET RECEPTOR AND A PLATELET RECEPTOR LIGAND

CROSS-REFERENCE TO RELATED APPLICATIONS

This is a continuation-in-part application of U.S. Ser. No. 11/484,364, filed Jul. 11, 2006 now abandoned.

TECHNICAL FIELD

The present invention relates generally to mimotopes and, in particular, to mimotopes for mimicking the receptor and inhibitor functionality of platelets.

BACKGROUND OF THE INVENTION

Mimotopes (mimetics or mimics) are molecules that mimic the function of other, naturally-occurring molecules by virtue of having the same shape (topography) and size as a fragment of/or of the interacting region of naturally-occurring molecules that they are mimicking. A method for determining mimotopes is described in U.S. Pat. No. 4,833,092 (Geysen).

As shown in FIG. 1a, a natural ligand has a particular shape and size that enables it to bind to a natural receptor. A mimotope ligand is a molecule that mimics the shape of the natural ligand and thus mimics its functional ability to bind to a natural receptor, as shown in FIG. 1b. In other words, a mimotope ligand is a molecule that is the topographical equivalent of a natural ligand (at least in terms of their binding surfaces) so as to be complementary to a particular receptor of interest.

A variety of ligand mimics are known in the art, which are used primarily as inhibitors or blockers, e.g. U.S. Pat. No. 4,550,163 (Voss et al.) entitled "Ligand analog-irreversible enzyme inhibitor conjugates" and U.S. Pat. No. 6,139,832 (Li et al.) entitled "Leukocyte adhesion inhibitor-1 (LAI-1) Polypeptides". Small peptides are also known as protein mimetics (see, e.g. Wrighton et al., "Small Peptides as Potent Mimetics of the Protein Hormone Erythropoietin" in *Science* (1996 Jul. 26; 273(5274):458-64). Mimetics of polypeptides used to detect antibodies are described in U.S. Pat. No. 6,858, 210 (Marquis et al.). Peptide mimics for backbone-to-backbone or backbone-to-chain cyclizations are described in U.S. Pat. No. 6,706,862 (Hornik).

In the context of platelets, mimotopes are also known as inhibitors of platelet adhesion and aggregation, such as described in U.S. Pat. No. 5,114,842 (Plow et al.) entitled "Peptides and Antibodies that Inhibit Platelet Adhesion". Specifically, Plow et al. teach a polypeptide analog capable of immunologically mimicking a linear hGPIIb antigenic determinant expressed when platelet-associated GPIIb-IIIa binds fibrinogen. Both U.S. Pat. No. 5,817,748 (Miller et al.) and its Continuation-in-Part U.S. Pat. No. 5,877,155 describe mimotopes and anti-mimotopes of human platelet glycoprotein IB/IX as well as a method for modulating platelet adhesion, aggregation or agglutination by exposing the platelets to an anti-mimotope in order to inhibit von Willebrand factor interaction with platelets through the glycoprotein Ib/IX complex receptor. However, these ligand mimics only perform an inhibitory (antithrombotic) function.

Although the foregoing represent useful advances in the art, further advances in platelet and antithrombotic technology remain highly desirable.

SUMMARY OF THE INVENTION

Accordingly, one object of the present invention is to provide more pharmacologically compatible mimotope inhibitors for a new class of antithrombotic drugs.

Another object of the present invention is to provide mimotope receptors, which would function either as inhibitors or which would be attached to a suitable carrier to constitute a synthetic or artificial platelet.

This invention relates to the creation of peptide mimics of platelet integrins and their ligands. Short peptides, usually between 10-20 mer, are designed to provide shapes complementary to either the receptor or the ligand. A shape that mimics an integrin receptor's binding surface can be used to mimic the integrin receptor's binding function. Attached to a supporting surface of a carrier, such a peptide can behave as a receptor. As a free molecule, such a peptide can attach to the ligand, preventing it from accessing the receptor, thus acting as an inhibitor of the receptor-ligand interaction. Similarly, a peptide that mimics the ligand's binding surface for the receptor will compete with the ligand and reduce its access to the receptor, thus also acting an inhibitor of receptor-ligand interaction. Such peptides may have, but are not obligated to have, sequence similarities to their parent proteins: they just need to have a complementary shape with sufficient binding affinity to attach to their counterpart in the receptor-ligand pair. Consequently, such peptides may be composed of L or D amino acids, although the D-amino acids are preferred as these resist proteolytic degradation.

Accordingly, one aspect of the present invention provides a mimotope receptor comprising a peptide that mimics the shape and function of a natural receptor, thus providing a synthetic binding site for ligands. As a free molecule, the mimotope receptor inhibits ligand-receptor interaction, e.g. acts as an antithrombotic in the context of platelet-platelet or platelet-endothelium interactions. If attached to a carrier, the mimotope receptor acts as a synthetic binding site, e.g. the carrier and mimotope receptor together function as a synthetic platelet.

Another aspect of the present invention provides a mimotope ligand comprising a peptide that mimics a natural ligand capable of binding to a receptor to thus inhibit ligand-receptor interaction, wherein the peptide is a D-peptide. Since the peptide is dextrorotary, it resists proteolytic degradation and thus forms the basis for a new class of antithrombotic drugs.

Yet another aspect of the present invention provides a mimotope ligand comprising a peptide that mimics a natural ligand capable of binding to a receptor to thus inhibit ligand-receptor interaction, wherein the peptide is attached to a large carrier. Since the peptide is attached to a carrier, it resists excretion, again forming the basis for a new class of antithrombotic drugs. In one embodiment, the peptide is also dextrorotary to resist proteolytic degradation.

Yet a further aspect of the present invention provides a synthetic platelet comprising a carrier and a receptor mimic attached to the carrier, the receptor mimic mimicking a shape and size of a binding site of a natural receptor on a natural platelet. A synthetic or artificial platelet (or "platelet substitute") would have virtually limitless shelf life and would not require disease screening prior to transfusion, thereby providing a solution to the perpetual platelet shortages, as well as the safety and storage issues associated with natural blood platelets.

According to another aspect, the present application provides a peptide mimotope capable of inhibiting an interaction between a platelet receptor and a platelet receptor ligand. In an embodiment, the platelet receptor is GPIb or GPIIbIIIa. In another embodiment, the platelet receptor ligand is von Willebrand factor or fibrinogen. In a further embodiment, the peptide mimotope is a receptor mimic. In still a further embodiment, the peptide mimotope is a ligand mimic. In still another embodiment, the peptide mimotope has a sequence consisting of the sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 16, SEQ ID NO: 17, SEQ ID NO: 18 or SEQ ID NO: 19. In another embodiment, the peptide mimotope is attached to a linker. In another embodiment, the linker consists of the sequence of SEQ ID NO:13. In yet another embodiment, the peptide mimotope is conjugated to a carrier, such as a liposome or an hyperbranched polyglycerol (HPG). In still a further embodiment, the peptide comprises at least one D-amino acid. In another embodiment, the peptide mimotope lacks amino acid sequence identity/similarity with the platelet receptor or the platelet receptor ligand. In still another embodiment, the peptide mimotope is capable of binding to one or more residues of the von Willebrand factor selected from the group consisting K549, W550, S562, H563, A564, Y565, I566, G567, L568, K569, B570, R571, E596, K599, Y600, P603, Q604, I605 and R632.

According to a further aspect, the present application provides a method of treating thrombocytopenia in an individual in need thereof. The method broadly comprises administering a synthetic platelet comprising the peptide mimotope described herein to the individual. In an embodiment, the concentration of the peptide mimotope administered to the individual is between 1 ug/kg to 0.3 mg/kg.

According to yet another aspect, the present application provides a method of limiting thrombosis in an individual in need thereof, said method comprises administering an antithrombotic drug comprising the peptide mimotope described herein to the individual. In an embodiment, the concentration of the peptide mimotope is about 1 mg/kg.

According to still a further aspect, the present application provides a method of identifying a receptor mimotope of a platelet receptor that can inhibit the interaction between the platelet receptor and a platelet receptor ligand. Broadly, the method comprises the steps of: (a) identifying a region in the platelet receptor that binds to the platelet receptor ligand; (b) selecting a random peptide fitting in the region identified in step (a); (c) contacting the random peptide of step (b) with the platelet receptor ligand; and (d) detecting the binding of the random peptide to the platelet receptor ligand. In this method, the binding of the random peptide to the platelet receptor ligand is indicative that the peptide is a mimotope inhibiting the platelet receptor and the platelet receptor ligand interaction.

According to still another aspect, the present application provides a method of identifying a ligand mimotope of a platelet receptor ligand that can inhibit the interaction between a platelet receptor and the platelet receptor ligand. Broadly, the method comprises the steps of: (a) identifying a region in the platelet receptor ligand that binds to the platelet receptor; (b) selecting a random peptide fitting in the region identified in step (a); (c) contacting the random peptide of step (b) with the platelet receptor; and (d) detecting the binding of the random peptide to the platelet receptor. In this method, the binding of the random peptide to the platelet receptor is indicative that the peptide is a mimotope inhibiting the platelet receptor and the platelet receptor ligand interaction.

BRIEF DESCRIPTION OF THE DRAWINGS

Further features and advantages of the present invention will become apparent from the following detailed description, taken in combination with the appended drawings, in which.

DESCRIPTION OF PREFERRED EMBODIMENTS

Figures 1A, 1B, 1C:
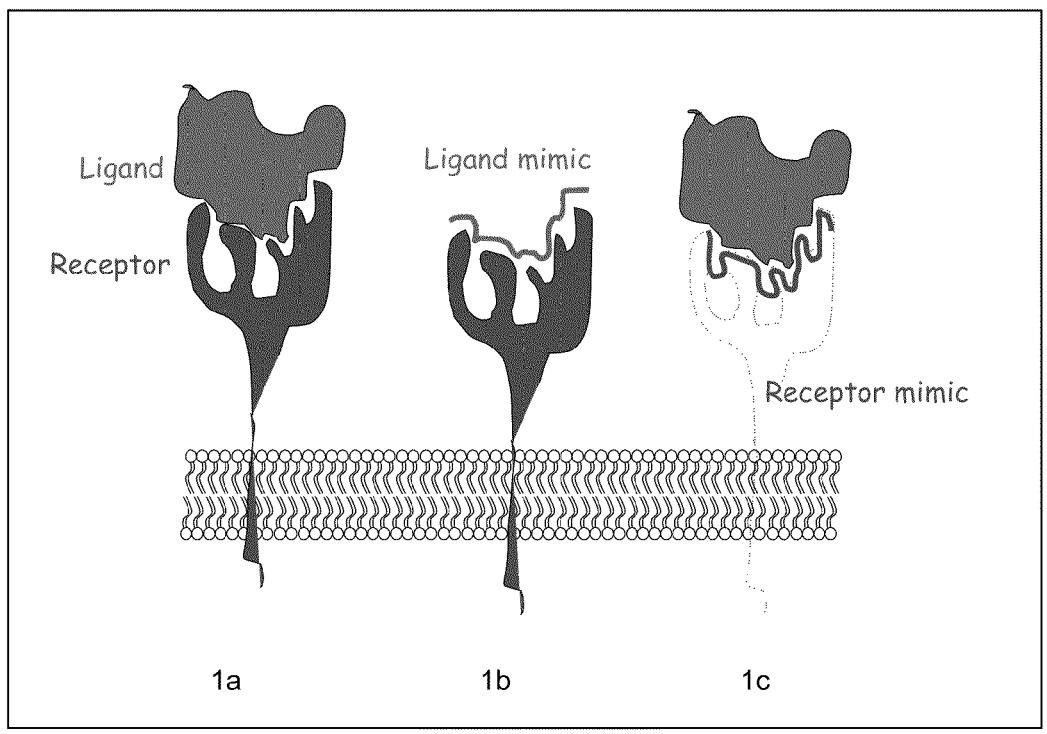
FIG. 1a is a schematic illustration of a ligand-receptor interaction between a natural ligand and a natural receptor.
FIG. 1b is a schematic illustration of a ligand mimic binding to a natural receptor, thus acting as an inhibitor of the ligand-receptor interaction, as is known in the art.
FIG. 1c is a schematic illustration of a peptide-based material that mimics the function of a receptor such as, for example, an integrin receptor on the surface of a platelet.

In general, and as will be elaborated below, embodiments of the present invention provide a peptide mimotope capable of inhibiting the interaction between a platelet receptor (such as an integrin) and its cognate ligand. In an embodiment, the platelet receptor is GPIb and its cognate ligand is the von Willebrand factor. The peptide mimotope can be a receptor mimic or a ligand mimic. Mimotope receptors can provide synthetic binding sites for ligands. Mimotope receptors can be attached to carriers, such as liposomes, hyperbranched polyglycerols or any other branched hydrophilic macro molecule available commercially with a number of arms, and arm lengths, to act as synthetic platelets, for example, by providing binding sites for binding to other (natural or synthetic) platelets or to the endothelium. Mimotope inhibitors can act as antithrombotics by inhibiting platelet-platelet and/or platelet-endothelium interactions.

More specifically, the mimotope peptide has an amino acid sequence as set forth in any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 SEQ ID NO: 16, SEQ ID NO: 17, SEQ ID NO: 18 or SEQ ID NO: 19. The mimotope can comprise exclusively L-amino acids, exclusively D-amino acids or a combination of both L- and D-amino acids.

In a further embodiment, the mimotope can be attached to a linker, which can be a peptide or other chemical structure of any length, such as, for example, 12 amino acids, such as the one having the sequence as set forth in SEQ ID NO: 13. In yet another embodiment, the mimotope can also be conjugated to a macromolecule, such as a liposome or an hyperbranched polyglycerol (HPG).

It is also provided a method of identifying a mimotope inhibiting the interaction between a platelet receptor and its cognate ligand. The method first comprises the steps of:
 a) identifying a region in the receptor or the ligand that is implicated in the receptor/ligand interaction;
 b) determining if a random peptide fits in this region (either on the receptor or the ligand side);
 c) contacting the random peptide with the receptor or the ligand; and
 d) detecting the binding of the random peptide with the receptor or the ligand, wherein binding of the random peptide to the receptor of the ligand is indicative that the peptide is a mimotope that inhibits the receptor/ligand interaction.

In an embodiment, the method disclosed herein can comprise the generation of overlapping peptides of the receptor or the ligand to determine the binding region of the receptor/ligand complex. Once generated, these peptides are probed with the receptor or the ligand to identify which peptides (or subregions) are important for the physical interaction between the receptor and its ligand (e.g. binding).

The method disclosed herein can further comprise the step of determining specific amino acids residues or even atoms involved in the interaction interface between the integrin receptor or its ligand prior to determining if the peptides fits in the region. In an embodiment, the MIAX paradigm can be used to determine atoms involved in the interaction interface between the platelet receptor ligand and the platelet receptor or to select the mimotope peptide.

In a further embodiment, the method comprises the step of determining in vitro if the random peptide binds to the receptor or the ligand. One way of determining binding consists of attaching the random peptide to a solid support (such as a cellulose membrane) before detecting the binding of the random peptide to the platelet receptor or its ligand. Another way of determining binding consists of a surface plasmon resonance assay (such as those using Biacore).

As shown in FIG. 1c, a peptide-based material can be used as a mimotope to mimic the form/shape (and thus the function) of a receptor. In one embodiment, the mimotope receptor (receptor mimic) can bind to a ligand to inhibit binding of the ligand to a natural receptor. In another embodiment, the mimotope receptor can be a peptide-based material that mimics an adhesion receptor or integrin on the surface of a platelet-like carrier like a liposome, preferably a cross-linked liposome.

In the context of platelets, an integrin, integrin receptor or (simply) receptor shall be used synonymously in the present specification to mean a molecule, such as a peptide or protein, on the surface of the platelet, embedded in the membrane of the platelet or on a carrier that selectively binds a specific molecule known as a ligand.

Figures 2A, 2B, 2C:
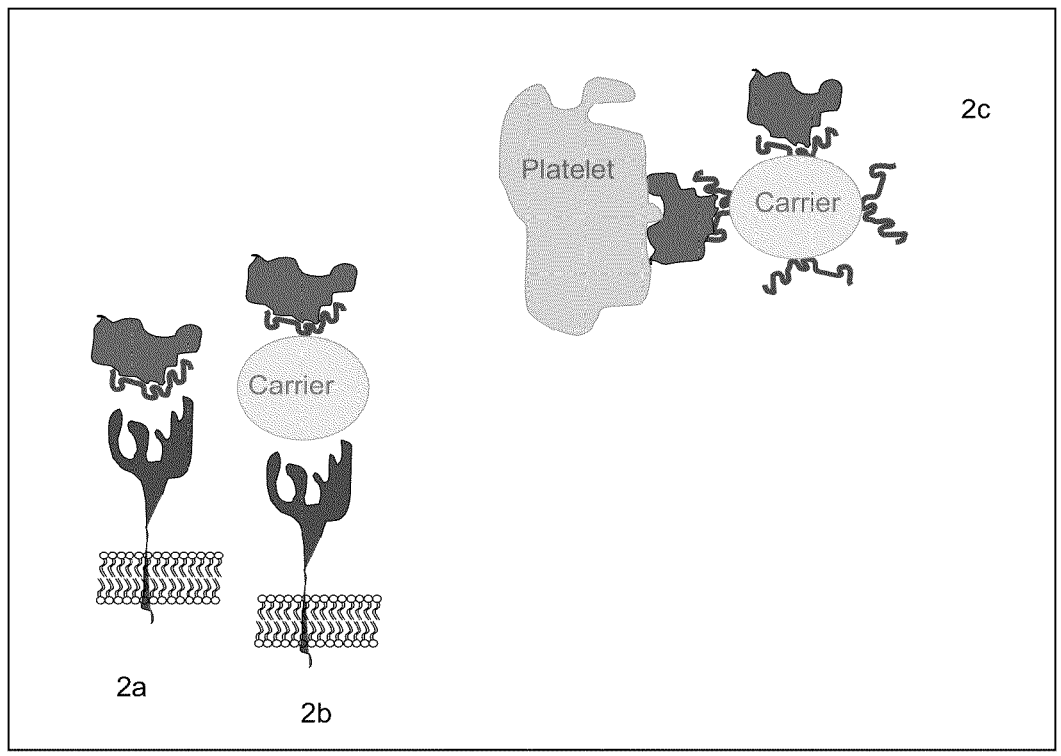
FIG. 2a is a schematic illustration of a mimotope receptor, a peptide-based material that, by specifically binding to the ligand like a receptor, can inhibit receptor-ligand interactions.
FIG. 2b is a schematic illustration of a mimotope receptor, a peptide-based material that, when attached to a large carrier at low coupling ratios, binds to the ligand to thus mimic a receptor, thereby providing a specific, quasi-monovalent inhibitory function such as, for example, functioning as an antithrombotic in the case of platelet-endothelium and platelet-platelet interactions.
FIG. 2c is a schematic illustration of a mimotope receptor, a peptide-based material that, when coupled to a large carrier at high coupling ratios, provides specific multivalent attachment possibilities, thus mimicking a receptor that is capable of binding multiple ligands.

As illustrated in FIG. 2a, a peptide-based material can be used as a receptor mimetic to bind to the ligand like a receptor, thus inhibiting receptor-ligand interactions. As shown in FIG. 2a, the mimotope receptor can be a "free" (unattached) peptide that has a shape/topology like that of a natural receptor so that it binds "preemptively" to ligands, thus preventing the ligands from binding to their natural receptors. These unattached, "free" receptor mimics thus act as inhibitors or blockers of the natural receptor-ligand interactions. In one embodiment, these mimotope receptors can be made of peptides that mimic the adhesion receptors or integrins of platelets. In the context of platelets, therefore, these unattached, "free" peptides would have an antithrombotic effect by binding to ligands and other coagulation factors, thus inhibiting e.g. normal platelet-platelet interaction.

As noted above, the mimotope receptor shown in FIG. 2a could be a peptide that mimics an integrin of a platelet. For example, the peptide mimic could be shaped to bind to a ligand such as one of the active sites of a von Willebrand factor (vWF) protein. In a basic vWF monomer (which is a 2050 amino acid protein), a number of specific domains are known to have specific functions. The A1 domain, for example, binds to the platelet GPIb receptor. The C1 domain binds to platelet integrin $\alpha_{IIb}\beta_3$ when activated. Therefore, in this example, the mimotope receptor could be a peptide that mimics the shape and structure of the binding site of platelet GPIb-receptor by binding preemptively to the A1 domain of the vWf monomer. Similarly, and again by way of example only, the mimotope receptor could be a peptide that mimics the shape and structure of the binding site of platelet integrin $\alpha_{IIb}\beta_3$.

The mimotope receptor shown in FIG. 2a could also be used to inhibit platelet-endothelium interaction by binding to the corresponding natural ligand that normally promotes adhesion of platelets to the vascular endothelial cells such as, for example, the von Willebrand factor protein. Thus, in this example, platelet-endothelium interaction can be inhibited by a mimotope receptor (peptide mimic) that binds preemptively to one of the active sites of the vWf protein to obstruct subsequent binding to that particular site on the vWf protein.

As illustrated in FIG. 2b, a peptide-based material can also be attached to a large carrier at low coupling ratios for providing monovalent or quasi-monovalent inhibitory functions. This mimotope is thus a monovalent receptor mimic which, whether attached to a carrier or not, can bind to a corresponding ligand, thus inhibiting receptor-ligand interactions. By mimicking a receptor, this mimotope provides a specific, quasi-monovalent inhibitory function that can be used, for example, as an inhibitor of platelet-platelet and platelet-endothelium interactions. This mimotope could thus be used as an antithrombotic.

As illustrated in FIG. 2c, a peptide-based material can be coupled to a large carrier at high coupling ratios to provide specific, multivalent attachment possibilities, i.e. the synthetic receptor can simultaneously bind a plurality of ligands. In this case, the mimotope mimics a multivalent receptor and thus can cross-link platelets and thereby form the basis of a synthetic platelet substitute.

In an embodiment, when the carrier is a liposome used to provide a platelet substitute, the (high) coupling ratio of the lipid:mimotope can be between about 20:1 to about 60:1, and preferably about 40:1. This can be achieved by mixing, for example, 10 mM of lipids with 150 μM of the mimotope. In this particulate embodiment, the peptide is coupled to the "outside" of the liposome. It is understood that, if a carrier of a different size is used, the ratio provided herewith will change in order to provide the synthetic platelet substitute.

As is known in the art, platelets (or "thrombocytes") are anuclear and discoid spherules ("flattened ellipsoids") that measure approximately 1.3-3.0 microns in diameter. Platelets adhere to each other via adhesion receptors or integrins and to the endothelial cells of blood vessel walls. Platelets form haemostatic plugs with fibrin, a clotting protein derived from fibrinogen.

A synthetic platelet can include a carrier, such as cross-linked liposomes, latex particles, agarose beads or hyperbranched polyglycerols that are manufactured to emulate some of the key physical characteristics of platelets (approximate size and shape, and resistance to liposome-cell fusion). The synthetic platelet can also include at least one receptor mimic attached to the carrier (i.e. the outer surface of the liposome). The receptor mimic can include a peptide that mimics a shape and size of a binding site of a natural receptor on a natural platelet. Preferably, the carrier can include a plurality of peptides attached to its outer surface, each one functioning as a receptor mimic to thus provide a "multivalent" synthetic platelet with multiple binding sites. In other words, each of the peptides is a mimotope that mimics a natural adhesion receptor or integrin found on a natural platelet.

Figures 3A, 3B:
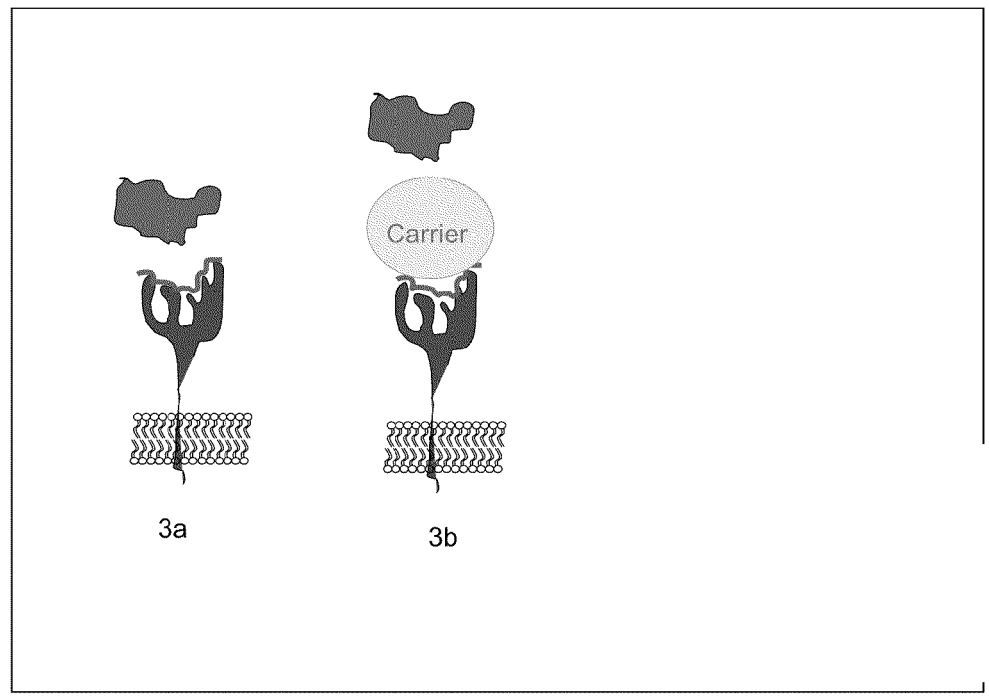
FIG. 3a is a schematic illustration of a mimotope ligand, a peptide-based material that can bind into an integrin receptor to thereby inhibit its ligand-binding function.
FIG. 3b is a schematic illustration of a peptide-based material that, when attached to a large carrier at a low coupling ratio, binds to the receptor, mimicking a ligand, and thus providing a specific, quasi-monovalent inhibitory function such as, for example, functioning as an antithrombotic in the case of platelet-endothelium or platelet-platelet interactions.

As shown in FIG. 3a, a peptide-based material comprising D-amino acids can be used to bind into an integrin receptor to thus inhibit its ligand-binding function. Although some L-peptides (levorotatory peptides) are known in the art, D-peptides (dextrorotary peptides) are preferred because they resist proteolytic degradation.

As shown in FIG. 3b, a peptide-based material can be attached to a large carrier (e.g. a liposome, vesicle or other body) at a low coupling ratio for binding to the receptor, thus mimicking a ligand and thus providing a specific, quasi-monovalent inhibition function (e.g. antithrombotic activity). For example, the monovalent ligand mimic interferes with ligand-receptor interaction and thus can serve as an antithrombotic in the case of platelet-platelet interactions or platelet-endothelium interactions. The peptide attached to the carrier can be levorotary (L) or dextrorotary (D). Attachment to the large carrier would resist excretion through the kidneys. In other words, the carrier (preferably a PEG, polyglycidol, or cross-linked liposomes) provides circulatory resistance and physical blocking or obstruction of the binding site In an embodiment, when a liposome is used as a carrier for the antithrombic composition, the (low) coupling ratio of the lipid:mimotope can be between about 100:1 to about 400:1. Preferably, the ratio can be about 400:1. In another embodiment, when HPG is used as a carrier for the antithrombotic composition, the coupling ratio of the HPG:mimotope is about 1:100. As known in the art, the use of carrier of different size will change the ratio effective for providing an antithrombotic composition.

A peptide-based material in accordance with one of the foregoing embodiments would have great utility in the context of an artificial platelet substitute or as an antithrombotic drug.

A peptide-based antithrombotic drug would resist proteolytic degradation (proteolysis) because it is made of D-amino acids which form peptide bonds that natural enzymes cannot break down. Furthermore, a peptide drug where the peptide is attached to a large carrier structure would resist excretion through the kidneys.

As platelets are routinely in short supply, it would be highly desirable to develop artificial platelets (also known as platelet substitutes). The advantages of artificial platelets are numerous, namely virtually indefinite shelf-life and easy storage. Moreover, artificial platelets would not require infectious disease testing or assessment to determine whether the platelets are still viable for transfusion. The technology described in the foregoing paragraphs would thus provide the "specificity" component for artificial platelets. In other words, the peptide mimotopes could be attached to a liposome or other (synthetic) platelet-like structure to form an artificial platelet capable of binding to other platelets, either real (natural) platelets or other artificial (synthetic platelets). Furthermore, the peptide mimotopes could be coupled to a carrier at low density (e.g. a quasi-monovalent interaction) to enable these peptides to function as platelet-inhibitors, thus giving rise to a new class of antithrombotic drugs.

In accordance with the present invention, a carrier or "pharmaceutical carrier" is a pharmaceutically acceptable solvent, suspending agent or any other pharmacologically inert vehicle for delivering one or more active compounds to a subject, and is typically in liquid form.

Compositions disclosed in the present invention may be administered with a pharmaceutically-acceptable diluent, carrier, or excipient, in unit dosage form. Conventional pharmaceutical practice may be employed to provide suitable formulations or compositions to administer such compositions to patients. The intravenous route of administration is preferred.

Methods well known in the art for making formulations are found in, for example, Remington: The Science and Practice of Pharmacy, (19th ed.) ed. A. R. Gennaro A R., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Other potentially useful parenteral delivery systems for agonists of the invention include ethylenevinyl acetate copolymer particles, osmotic pumps, implantable infusion systems, and liposomes.

In addition, the term "pharmaceutically effective amount" or "therapeutically effective amount" refers to an amount (dose) effective in treating a patient. It is also to be understood herein that a "pharmaceutically effective amount" may be interpreted as an amount giving a desired therapeutic effect, either taken in one dose or in any dosage or route, taken alone or in combination with other therapeutic agents.

A therapeutically effective amount or dosage of a mimotope disclosed herein or a pharmaceutical composition comprising the mimotope, may range from about 0.01 µg/kg to 3 mg/kg body weight, with other ranges of the invention including about 1 mg/kg.

It is obvious for those skilled in the art that as the technology develops the basic idea of the invention can be implemented in various ways. The invention and the embodiments thereof are thus not restricted to the examples described above, but they may vary within the scope of the claims.

The present disclosure will be more readily understood by referring to the following examples which are given to illustrate embodiments rather than to limit its scope.

Example I

Production and Characterization of a GIb-Binding vWf Ligand Mimotope

The von Willebrand factor (vWf) amino acid sequence and available literature were used to select the potential vWf binding site for the integrin, glycoprotein Ib (GPIb). As is known in the art, von Willebrand factor (vWf) is a large multimeric blood glycoprotein present in blood plasma that plays a significant role in blood coagulation. The vWf is produced in the Weibel-Palade bodies of the endothelium, in megakaryocytes (α-granules of platelets), and in subendothethial connective tissue. The primary function of von Willebrand factor is binding to other proteins, such as Factor VIII, binding to collagen, binding to platelet gpIB, and binding to other platelet receptors when activated, e.g. by thrombin.

The vWf amino acid sequence was used to generate 10-mer L-amino acid overlapping peptides, shifted by two (2), according to the following pattern:

```
ACDFGHIKWER        (SEQ ID NO: 1)
DFGHIKWERAL        (SEQ ID NO: 2)
GHIKWERALND        (SEQ ID NO: 3)
```

These peptides were synthesized and remained attached on the cellulose membrane. The membranes were probed by purified GPIb which was detected by anti-GPIb coupled to horseradish peroxidase (HRP). A number of positive spots were found whose sequences were derived from their positions on the membrane.

Figure 4:
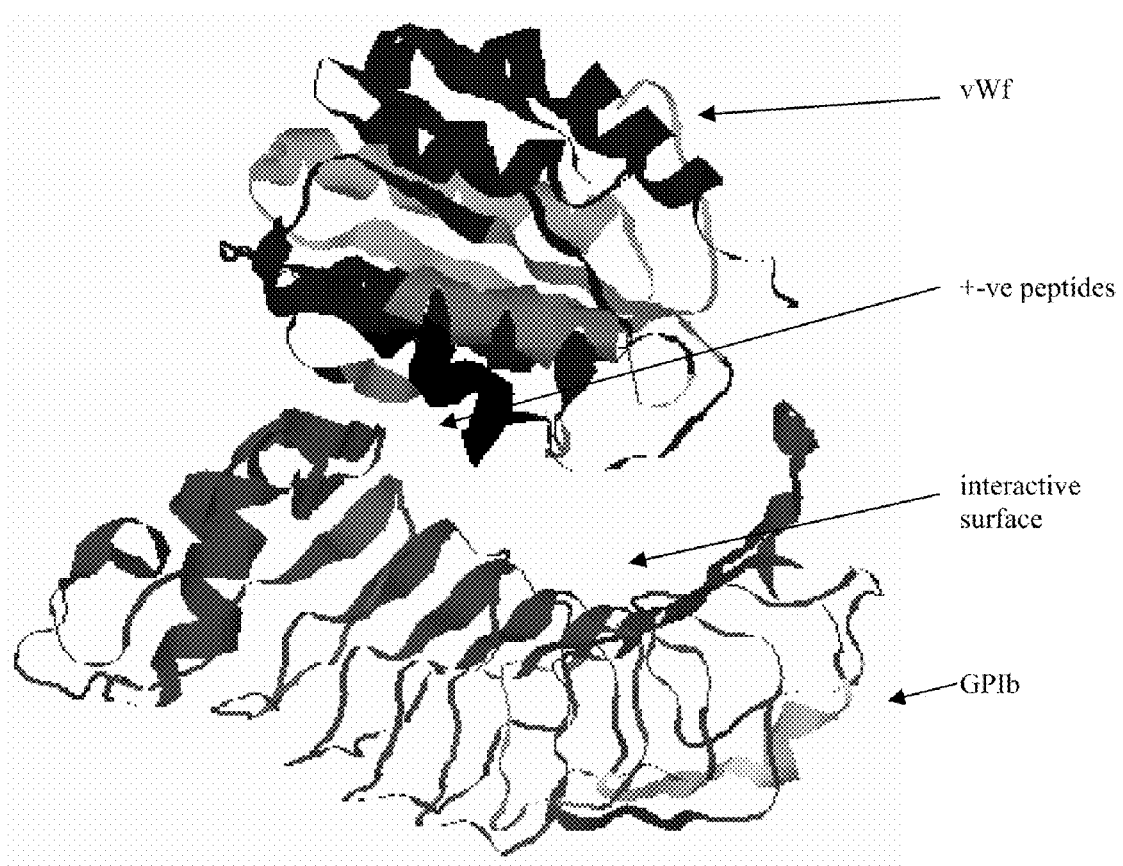
FIG. 4 shows a 3D computer model of a parent protein used for finding positions of particular sequences to enable the position to be related to potential vWf-GPIb interaction sites.

The sequences were analyzed in silico by (a) finding their positions in a 3D model of the parent protein (see FIG. 4) and then (b) relating that position to the potential vWf-GPIb interactive site. This suggested that the peptides colored black (identified in FIG. 4 as "+−ve peptides") were in the interactive region and thus, as free peptides, could serve as competitive inhibitors of the interaction.

A similar study was conducted using overlapping peptides of the GPIb molecule, but the positive peptides identified by colors (in FIG. 4) contributed relatively little to the interactive site.

This series of experiments identified a number of vWf native sequences of L-amino acids with potential inhibitory activity for the GPIb-vWf interaction.

Figure 5:
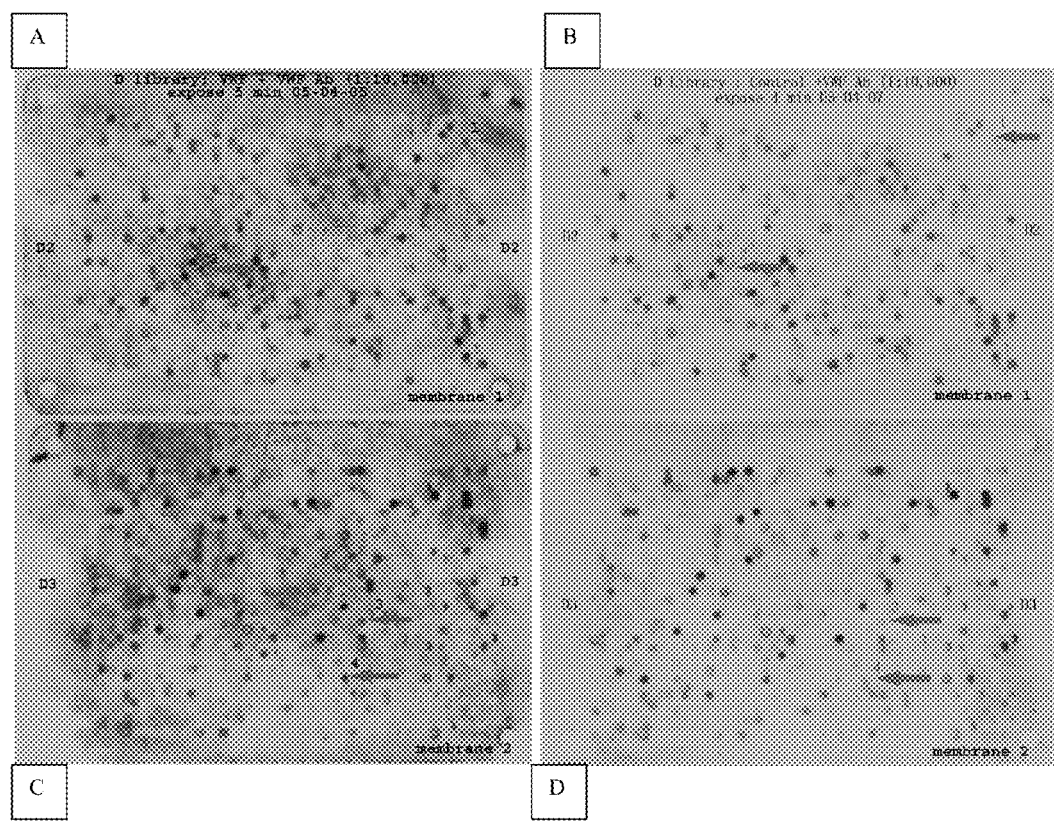
FIG. 5 shows four cellulose membranes to which peptides were attached and which were then probed with purified vWf in order to identify sequences of d-amino acids which potentially mimic GIb and thereby can inhibit the GPIb-vWf interaction. Panels A and C correspond to the positive panels that were probed with vWf, then vWf-binding was identified by anti-vWf antibodies coupled to peroxidase. The arrows indicate the specific binding, positive spots. Panels B & D are the corresponding controls; the same sequences/spots were probed with anti-vWf-peroxidase only. In panels B & D, the arrows show the empty areas where spots were present on the test panels, but not present on the controls.

Random D-amino acid peptides (15 mer) were synthesized and probed with vWf to detect random sequences capable of binding vWf. FIG. 5 shows the membranes from which four positive sequences were derived.

Figure 6:
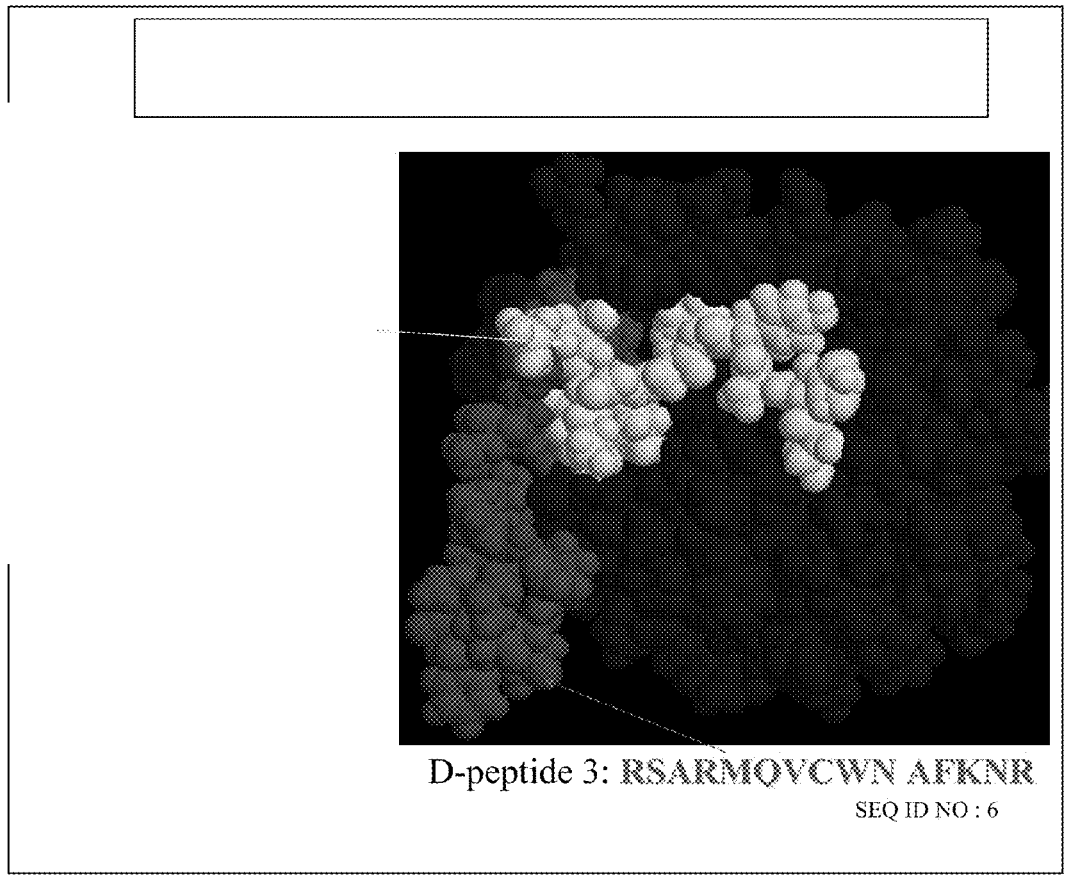
FIG. 6 shows the confirmatory structural results of 3D computer modeling of the interaction between a random peptide (D-peptide 3 or SEQ ID NO: 6) and vWf.

To determine whether these peptides were complementary to the binding surface defined by the GPIb molecule, they were analyzed in silico by (a) comparing them to known sequences in PDB.A. Fasta search provided homologues/decoys of known structure, (b) then the structures were docked onto the vWf molecule to check for 3D fit. The confirmatory structural results of this analysis for D-peptide 3 (SEQ ID NO: 6) are shown in FIG. 6. More specifically, it was proposed that D-peptide 3 (SEQ ID NO: 6) binds to residues SER562, HIS563, ALA564, TYR565, ILE566, GLY567, LEU568, LYS569, ASP570 and ARG571 of the vonWillebrand factor. The energy of this interaction was estimated at 432.53 Kcal/mol.

Thus, the structural analysis by computer confirms the physical findings that random D-amino acid peptides that are structurally complementary (in this case to vWf) are also those that can be demonstrated experimentally to bind in vitro.

Example II

Production and Characterization of GPIIbIIIa Receptor Mimotope

Figure 7:
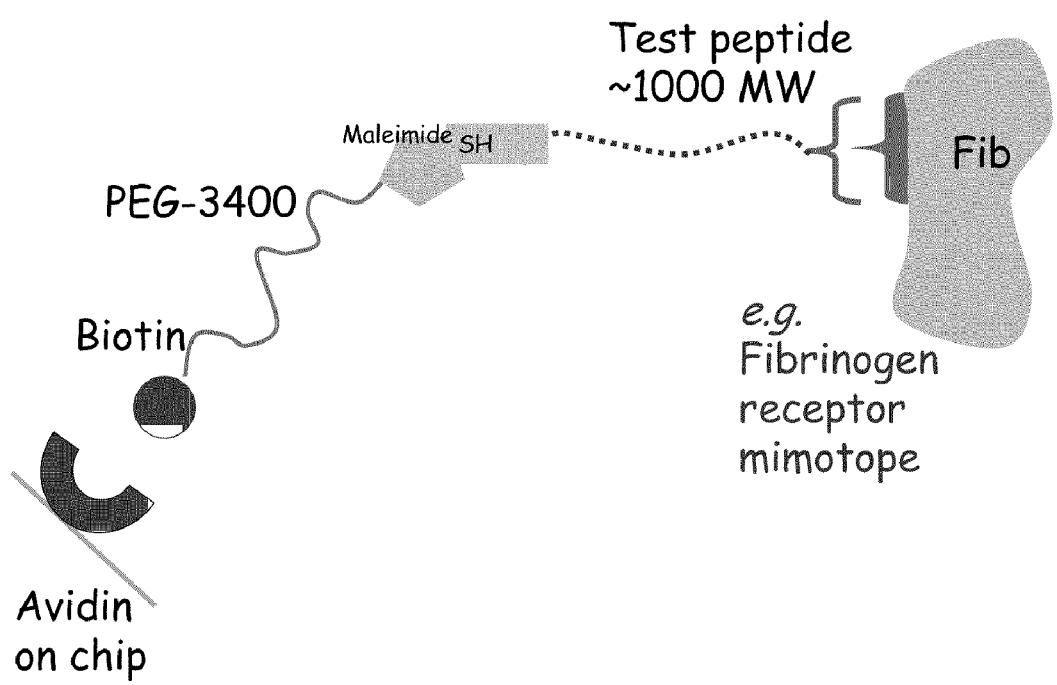
FIG. 7 shows schematically how surface plasmon resonance in a Biacore machine can be used to validate that the peptides can act as receptors/binding partners.

To confirm that peptides can act as receptors/binding partners, not just as inhibitors, real-time binding was demonstrated by surface plasmon resonance in a Biacore machine. In this case, peptides known to interfere with fibrinogen-GPIIbIIIa interaction were synthesized, and coupled to the end of a long (3400 MW) PEG molecule whose other end was attached to biotin, as illustrated schematically in FIG. 7. As is known in the art, fibrinogen is a soluble protein in the blood plasma essential for clotting of blood which the enzyme thrombin converts into the insoluble protein fibrin. As shown schematically in FIG. 7, the biotin molecule was used to tether down the peptide-PEG onto a streptavidin-modified Biacore chip. This allowed the GPIIbIIIa mimicking peptide to be hanging off the free end of the PEG.

By allowing free fibrinogen to flow past the peptide, the binding kinetics (i.e., the "on/off rate") between fibrinogen and the peptides were measured. Then, the fibrinogen was released from the peptide. Using several fibrinogen concentrations, it was possible to measure the KD of the binding interaction between the peptide and the fibrinogen.

Figure 8:
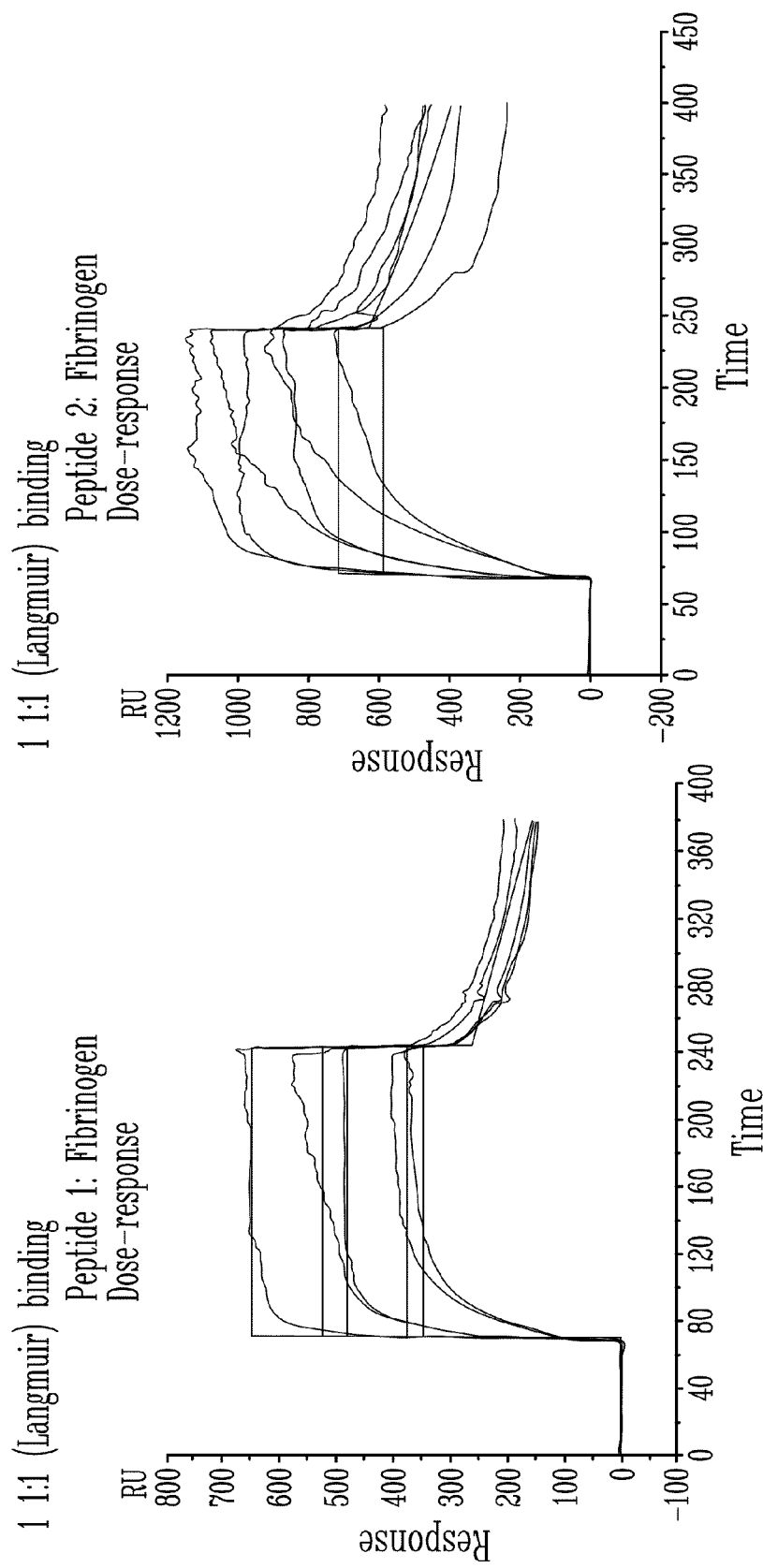
FIG. 8 shows a Langmuir binding analysis used to determine the KD of the binding interaction between two different GPIIbIIIa mimotopes and fibrinogen (A—peptide 1, B—peptide 2).

The Langmuir binding analysis is shown in FIG. 8. More specifically, FIG. 8A shows results obtained with GPIIbIIIa mimotope peptide 1 (APLHK; SEQ ID NO:14) having a $K_d$ (M) of $1.25^{-5}$. FIG. 8B shows results obtained with GPIIbIIIa mimotope peptide 2 (EHIPA; SEQ ID NO:15) having a $K_d$ (M) of $3.34^{-7}$. The $K_d$ (M) of wild-type GPIIaIIIb with fibrinogen is $1.03^{-7}$.

A number of D-amino acid-containing sequences have also been generated and tested for their ability to bind to fibrinogen. Peptides having the following sequences SMTSMCYLIGAPKYK (SEQ ID NO:16); KYQCYAPAHPSYVNY (SEQ ID NO:17); FKWSWEWQGQEAYYD (SEQ ID NO:18); and FRIYYVYTTSQQDSC (SEQ ID NO:19) have been shown to bind to fibrinogen. These peptides can be used to pull/capture fibrinogen from a solution as well as to inhibit the interaction between fibrinogen and its cognate receptor(s).

This showed that a peptide can generate binding kinetics/affinities similar to that of the parent protein and thus confirms the concept that peptides can act as synthetic receptor molecules.

The novel concept of using a peptide as a receptor mimic rather than only as an inhibitor opens a whole new potential field in the realm of peptide array and drug delivery.

A synthetic receptor bestows a number of significant advantages. First, since the receptor is synthetic, it does not have to be extracted, or made out of living material, purified, cleaned, etc. Second, it can be made (designed) to carry out any receptor function as long as the three dimensional shape of the receptor is mimicked. Third, the future production of synthetic cells (or cell-replacing materials) would require synthetic receptor functionality and thus a synthetic receptor would be a very significant first step in creating synthetic cells or synthetic platelets.

Potential uses of a synthetic receptor are numerous. As mentioned above, a synthetic receptor can be used on a platelet substitute (i.e. a synthetic or artificial platelet). Furthermore, the synthetic receptor can be used to offer a specific binding capacity for isolating and analyzing ligand molecules without the need for monoclonal antibodies. These synthetic receptors could thus replace monoclonal antibodies in assay systems currently relying on monoclonal antibody technology. This would thus potentially eliminate the need for culturing and maintaining specific antibody-producing clones.

Moreover, the synthetic receptors can be tailored to obtain defined kinetics and binding affinities. The synthetic receptors could also be made from D-amino acids, thereby preventing or retarding in vivo proteolysis.

Example III

Rational Design of Antithrombotic Peptides

The design a mimotope that would exert GPIb-like receptor function and antithrombotic function by inhibiting the GPIb-vWf protein-protein interaction was conducted. To do this, first, using bioinformatics, atoms involved in the interaction interface between GPIb and vWf were determined. Next, using classical laboratory methods, peptides from a random D-peptide library were selected by their ability to bind to purified vWf. Returning to the computer, the site of the peptides' interactions was then confirmed with vWf. Four peptides that best occupied a region within the GPIb-vWf recognition interface were selected.

Commercial software for computational methodologies that allow these types of evaluations is not available; therefore, the study disclosed herein was carried out using a suite of novel programs developed. Central to this collection of computational procedures is the MIAX paradigm (Macromolecular Interaction Assessment computer system) (Del Caprio et al., 2002, Proteins: Structure, Function and Genetics, 48: 696-732) which enables the prediction of the most probable configuration of protein-protein, protein-peptide, and other bio-macromolecular complexes in solution. It combines in a rational way a series of computational methodologies, the goal being the prediction of the most native-like protein complex that may be formed when two isolated (unbound) protein monomers interact in a liquid environment. The overall strategy consists of first inferring putative pre-complex structures by identification of binding sites or epitopes on the proteins' surfaces and a simultaneous rigid-body docking process using geometric instances alone. Pre-complex configurations are defined here as all those decoys of which the interfaces comply substantially with the inferred binding sites and whose free energy values are the lowest.

Retaining all those pre-complex configurations with low energies leads to a reasonable number of decoys for which a flexible treatment is amenable. MIAX is endowed of novel algorithm for automatically inferring binding sites in proteins given their 3-D structure. The procedure combines an unsupervised learning algorithm based on the self-organizing map or Kohonen network with a 2-D Fourier spectral analysis. To model interactions, the potential function proposed here plays a central role in the system and is constituted by empirical terms expressing well-characterized factors influencing bio-macromolecular interaction processes, essentially electrostatic, van der Waals, and hydrophobic ones. Each of these procedures has been validated by comparing results with observed instances. Finally, the more demanding process of flexible docking is performed in MIAX embedding the potential function in a simulated annealing optimization procedure.

MIAX was used to analyze and predict biomolecular structures, assess and infer inter-macromolecular interactions, and assist the rational process of drug design. The latter process is epitomized by the ability of the system to infer and thus assist in the design of complementary peptides to protein active sites particularly those located within the interface of protein-protein interactions. MIAX is oriented to the holistic analysis of the structure and function of proteins and other bio-molecules translated in their interaction patterns with other protein subunits or other biomacromolecules as well as with small organic compounds.

MIAX was applied to the complex of GPIb integrin and its ligand, vWf, found in the Protein Data Bank (PDB:1SQ0) and analyzed the GPIb-vWf system to determine the characteristics of the interaction interface of the resulting complex.

Characterization of the Interaction Interface of the GPIb-vWf Protein Complex

Figure 9:
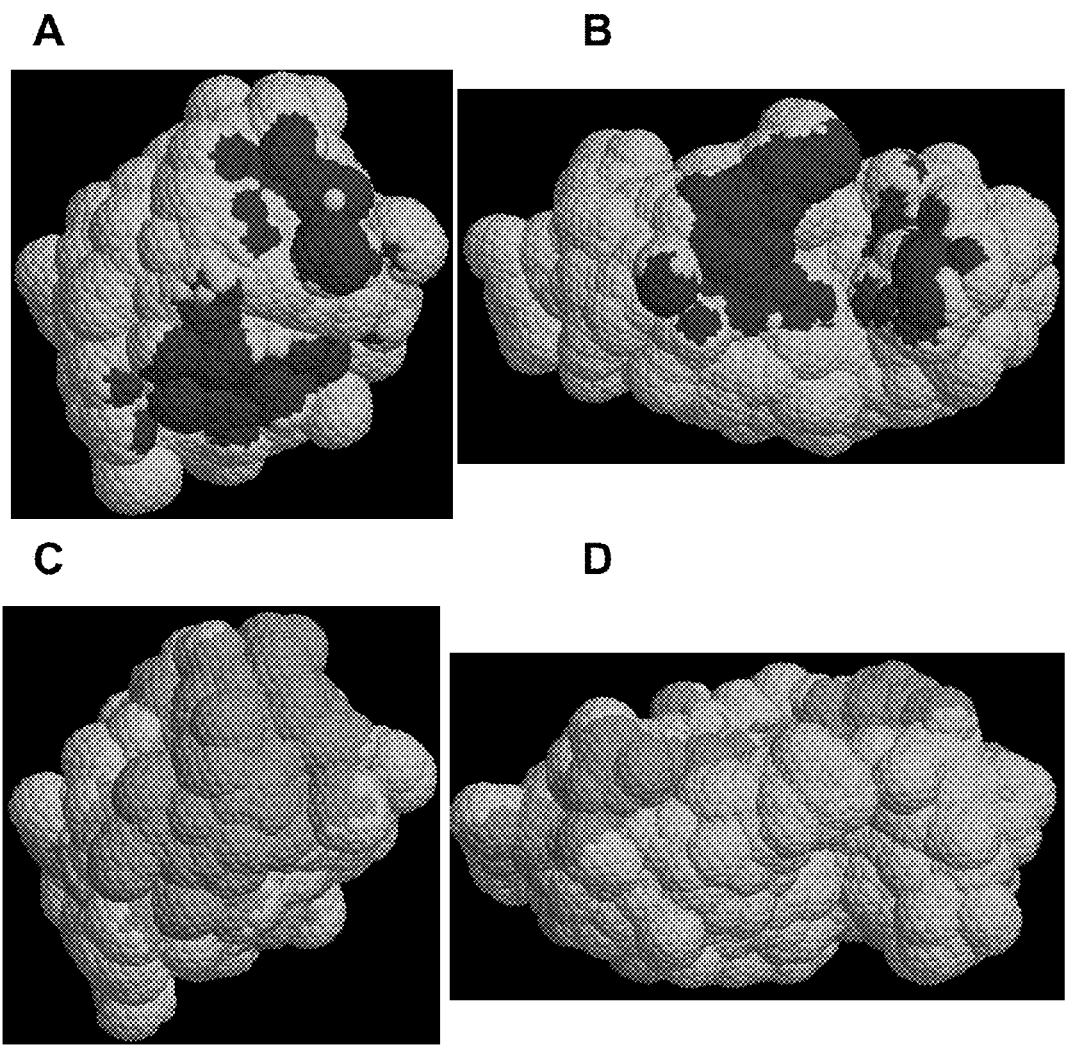
FIG. 9 shows the representation of the composition of the interaction interface of vWF complex (A) and GPIb complex (B) and the hydrophobic patches on the subunits of the vWF (C) and GPIb (D) complex.

Characterization of the interaction interface for the GPIb-vWf complex is performed by computing the decrement in surface area of the subunits at complex formation. SASA (solvent accessible surface area) is computed with a water molecule radius of 1.4 A. The amino acids differences in SASA identify them as those involved or not in the interaction interface. Computing distances between atoms belonging to different units in the interaction allows inference of particular interactions between the units such as hydrogen bonds, electrostatic interactions or hydrophobic interactions, which can be compared with reported interactions or with those in the entries of interaction databases. The result is shown in FIG. 9 where the interaction surfaces are mapped on each of the subunits constituting the complex GPIb-vWf (FIG. 9A: vWf, FIG. 9B: GPIb).

Physicochemical Characteristics of the Interaction Interfaces

Physicochemical characteristics of the interacting subunits (interacting proteins and peptides) are computed by means of the SOM-MIAX module in MIAX. The main physicochemical characteristic computed for GPIb-vWf is the relative hydrophobocity of regions on the proteins surfaces. The calculation uses the molecular hydrophobic potential introduced by Brasseur (Brasseur, 1991, J Biol Chem, 266: 16120-16127), and a learning algorithm that incorporates the self-organized maps of Kohonen (Kohonen, 1990, Proceedings IEEE, 78: 1464-1480). Image processing is applied to define the limits of the hydrophobic patches on the surfaces of the interacting units.

Generation of Inhibitory Peptide Sequences

Random peptide arrays of 1120 peptides made of D-amino acids were synthesized on a cellulose membrane using an AutoSpot ASP 222 peptide synthesizer (ABiMED, Langenfeld, Germany). Resulting replicate libraries of 15-mer sequences were probed for vWf binding function by exposing the membranes to purified vWf after blocking with skim milk to prevent non-specific binding of horseradish peroxidase labelled goat anti-human-vWf IgG. The chemiluminescent substrate from the Amersham Pharmacia ECL kit detected positive spots that were recorded on photographic film. Negative controls consisted of probing the membranes with the antibodies without prior exposure of the membrane to purified vWf.

Modeling the 3D Structures of the Designed Peptides

The three dimensional structures (3D) of peptides can be determined by ab initio calculations such as the GAX system (Del Carpio, 1996, Journal of Chemical Information and Computer Sciences, 36: 25-269). This is a robust methodology to build 3D structures of the peptides designed to bind vWf. The Brookhaven Protein Data Bank was scanned for segments of high similarity to the sequences of the selected peptides. A FASTA search identified highly similar sequences and their structures were used as the initial conformations for the peptides. The 3D structures underwent a change from the L conformation to the D conformation and a series of minimizations and Molecular Dynamics simulations produced the most energetically stable conformations for the peptides in solution. These were performed using the force fields in AMBER-6 (Ponder and Case, 2003, Advances in Protein Chemistry, 66: 27-85).

Docking of the Peptides to a Receptor Using MIAX

With the 3D structures of the interacting molecular entities, the docking module of MIAX computed the complexes they may form when they interact. MIAX is endowed with three types of modules for docking macromolecules: a rigid body docking module to discover interaction pathways when the structure of the complex is known a priori; a "soft docking" module, that docks two units of which the structures are known only in the isolated state. This being the present case, this module was applied first to dock the peptides to vWf. The third module in MIAX is characterized by the flexible docking of units, in which there is a rigorous analysis of the conformation of the side chains of interface amino acids. MIAX performs the docking taking into account the geometry of the molecules as well as the interaction energy of the system.

Geometric characteristics of the interacting subunits are considered by a discretization process of the molecular bodies and performing a grid point complementarity analysis of the subunits and their fit into 3D space [11]. The interaction energies are computed by the following expression:

$$\Delta G^{AB(s)} = E_{hy} + E_{elec} + E_{hb} + E_{tor} + E_{desol} \quad (1)$$

where $\Delta G^{AB(s)}$ is the change in free energy at complex formation in solution, and the terms on the right stand for the hydrophobic energy ($E_{hy}$), electrostatic interaction ($E_{elec}$) hydrogen bonding ($E_{hb}$), torsional energy ($E_{ton}$) and the energy of desolvation ($E_{desolv}$). Each of these terms is described in detail elsewhere.

Molecular Dynamics Simulation of the Complexes to Compute Complex Stability

The stability of the complexes obtained by the MIAX docking process was tested by means of molecular dynamic simulations using the AMBER-6 force field. The simulation was performed in vacuum and for 50 ps for each of the complexes. The second objective of this simulation is to detect any major change in the conformation of the subunits, eg changes in the interaction interface that may lead to improved accommodation of the peptide on vWf.

Characterization of Peptide-vWf Interaction Interfaces and Validation of the Selected Peptides Characterization of the interaction interfaces of the candidate conformations (decoys) for the peptide-vWf complex output by MIAX followed by the molecular dynamics experiment was done as for computing the interaction interface of GPIb-vWf complex. The decrement of SASA of atoms constituting the peptides and vWf led to the map of the interface in terms of the interacting atoms. Visualization of the interface and identification of the main interactions such as hydrogen bonding and hydrophobic interactions were displayed using the LIGPLOT system (Wallace et al., Protein Engineering, 8: 127-134).

Inhibition of GPIb-vWf-Mediated Platelet Agglutination

Peptides on random 15-mer peptide arrays that were built of D-amino acids were selected on the basis of their ability to bind to vWf. Only four positive sequences were identified: D-pep1—VSRQNGKQYWAIKEG (SEQ ID NO:4); D-pep2—WQNEGTHVLSRCYEC (SEQ ID NO:5); D-pep3—RSARMQVCWNAFKNR (SEQ ID NO:6); and D-pep4—DSCPRDWDNNFLFFE (SEQ ID NO:7). D-pep2 (SEQ ID NO:5), D-pep3 (SEQ ID NO:6) and D-pep4 (SEQ ID NO:7) were synthesized for laboratory experimentation. D-pep3 (SEQ ID NO:6), 10 mg, was synthesized by UBC's Peptide Proteomic Centre and was solubilized in Hepes-saline buffer, pH 7.4 and used at 0.1-0.5 mg/mL. Fresh washed platelets (160×10$^8$/mL) in Hepes buffer were added and agglutination was initiated by 1.25 mg/mL ristocetin (Sigma). Agglutination times and levels were monitored both microscopically and on an aggregometer (ChronoLog) as described by the manufacturer.

One of the most important properties driving proteins to interact with each other is the hydrophobicity of their surfaces. This physicochemical characteristic of the protein surface is usually expressed in terms of the number of hydrophobic amino acids present in particular regions of the molecular surface. Here, a series of calculations were performed in order to obtain these regions, using the SOM module in MIAX. The learning steps were set to 6000, and the filtering coefficient was set to 5. The results are shown graphically in FIGS. 9c and 9d.

A careful inspection of the list of amino acids of the hydrophobic patch on vWf (K549, W550, S562, H563, Y565, R571, I580, E596, K599, Y600, P603, Q604, I605, P606, S607, R611, E613, R632) with those involved in the interaction with GPIb: K549, W550, S562, Y565, E596, K599, Y600, P603, Q604, I605, R632 (FIGS. 9c & 9d) shows that all of the computed interactive amino acids are present in the hydrophobic patch (concordances in bold). Furthermore, experimental studies by Shimizu et al. (2004, J Biol Chem, 279: 16285-16294) as well as those of Hauert et al. (2004, Chem Bio Chem, 8: 856-864) established the importance of several of these amino acids by mutation assays that led to inhibition of the protein interaction between GPIb and vWf. They focus especially on amino acids R571, E613, K599 through P611 and R632, coinciding to a high degree with the computed results obtained here.

Three dimensional structures for the experimentally selected peptides were modeled according to the methodology described hereinabove (see Table 1).

In Table 1, the sequence of each peptide is shown together with the most similar sequence derived by a FASTA protein comparison search from PDB. The backbone of such a peptide was used as the starting backbone structure for each peptide before molecular dynamics simulation. Table 1 also summarizes the energies of the D-peptides after undergoing the conformation shift and the MD simulation process until energy convergence was achieved, as well as energies after minimization of the MD derived peptide structures, this procedure is performed in order to obtain the most realistic conformation for each peptide in solution.

TABLE 1

Characteristics of the D-Peptide Conformation Modeling Process

| PEPTIDES | D-pep1 | D-pep2 | D-pep3 | D-pep4 |
|---|---|---|---|---|
| Sequence | VSRQNGKQY WAIKEG (SEQ ID NO: 4) | WQNEGTHVL SRCYEC (SEQ ID NO: 5) | RSARMQVCW NAFKNR (SEQ ID NO: 6) | DSCPRDWDN NFLFFE (SEQ ID NO: 7) |
| FASTA output of most similar sequence | I50-G64 of PDB: 1XSX | D141-C155 of PDB: 1M8Y | R13-K27 of PDB: 1W81 | P31-L45 of PDB: 1A88 |

TABLE 1-continued

Characteristics of the D-Peptide Conformation Modeling Process

| | | | | |
|---|---|---|---|---|
| Energy of D-peptide after conformation change and MD (kcal/mol) | 595.81 | 140.19 | 55.49 | 141.49 |
| Energy of D-peptide after minimization (kcal/mol) | −777.22 | −397.87 | −954.67 | −895.43 |

| COMPLEXES | vWf-D-pep1 | vWf-D-pep2 | vWf-D-pep3 | vWf-D-pep4 |
|---|---|---|---|---|
| Energy vWf (kcal/mol) | −3350.00 | −3350.00 | −3350.00 | −3350.00 |
| Energy Complex (kcal/mol) | −4870.12 | −4220.2 | −5110.2 | −5460.31 |
| BE (kcal/mol) | −742.90 | −472.33 | −805.53 | −1124.88 |

Table 2 shows the inter-unit hydrogen bonds computed using the HYPLUS (Xu et al., 1997, Protein Engineering 10: 999-1012) system and summarizes the characteristics of the hydrogen bonds at the interface. The main characteristics shown are the polypeptide chains (A for vWf and B for GPIb), the number of the amino acids involved in the hydrogen bond as donor and acceptor, and the PDB names of the donor and acceptor atoms. Additionally, the Donor-Acceptor distance (D-A), the hydrogen acceptor (H-A), and the respective angles are also disclosed in Table 2.

TABLE 2

Characteristics of the intermolecular hydrogen bonds of the vWf-GPIb complex

| DONOR | | ACCEPTOR | | Dist | DHA[e] | | Dist. | Angles H-A-AA | D-A-AA |
|---|---|---|---|---|---|---|---|---|---|
| Amino Acid | Atom | Amino Acid | Atom | D-A | dist | angle | H-A | | |
| [a]A0549[b]-LYS[c] | NZ[d] | B0005-GLU | OE1 | 3.32 | 11.79 | 170 | 2.33 | 99.8 | 100.2 |
| A0562-SER | N | B0239-MET | O | 2.91 | 5.39 | 160 | 1.95 | 146.8 | 150.2 |
| B0239-MET | N | *A0562-SER | O | 3.01 | 5.39 | 148 | 2.11 | 145.3 | 154.9 |
| A0564-ALA | N | B0237-LYS | O | 3.21 | 5.29 | 167 | 2.22 | 128.5 | 126.5 |
| B0237-LYS | N | A0564-ALA | O | 3.04 | 5.29 | 153 | 2.12 | 134.6 | 142.8 |
| A0571-ARG | NE | B0018-ASP | OD2 | 2.91 | 9.38 | 166 | 1.93 | 138 | 134.9 |
| *A0571-ARG | NH2 | B0039-SER | OG | 2.87 | 10.86 | 109 | 2.39 | 130.2 | 136.5 |
| B0228-TYR | OH | *A0596-GLU | OE1 | 2.91 | 11.22 | 171 | 1.92 | 103.6 | 102.6 |
| *A0599-LYS | NZ | B0198-PRO | O | 3.13 | 8.6 | 157 | 2.19 | 123.5 | 123.7 |
| A0599-LYS | NZ | B0228-TYR | OH | 2.86 | 12.57 | 159 | 1.9 | 115.7 | 116.7 |
| B0152-LYS | NZ | A0603-PHE | O | 3.01 | 9.7 | 157 | 2.06 | 127.9 | 133.8 |
| *A0604-GLN | NE2 | B0176-THR | OG1 | 2.85 | 8.54 | 164 | 1.87 | 147.2 | 145.4 |
| *A0632-ARG | NH2 | B0225-GLU | OE1 | 2.52 | 11.09 | 119 | 1.88 | 120.9 | 112.2 |

[a]Subunit: A = vWf, B = GPIb
[b]Amino acid number within the subunit
[c]Amino acid name
[d]Atom name
[e]DHA (Donor, Hydrogen, Acceptor)
*Homolog hydrogen bonds, found in the vWf-GPIb complex and in the vWf-peptide complexes below.

Table 3 shows the energies of the complexes after the energy minimization procedure. Binding energy (BE) calculated as:

$$BE = E(\text{complex}) - [E(vWf) + E(D\text{-peptide})] \quad (2)$$

was computed for each complex to evaluate the stability of the derived species.

TABLE 3

Characteristics of the intermolecular hydrogen bonds for each of the vWf D-pep complexes

| DONOR | | ACCEPTOR | | Dist | DHA | | | Angles | |
|---|---|---|---|---|---|---|---|---|---|
| Amino Acid | Atom | Amino Acid | Atom | D-A | dist | angle | DistH-A | H-A-AA | D-A-AA |
| vWf - D-pep1 (SEQ ID NO: 4) | | | | | | | | | |
| 0004-GLN | NE2 | *A0562-SER | O | 2.96 | 7 | 120 | 2.34 | 120.7 | 137.4 |
| B0001-VAL | N | A0563-HIS | NE2 | 3.17 | 5.57 | 152 | 2.24 | 103.1 | 92.6 |
| B0002-SER | OG | A0565-TYR | OH | 3.29 | 7.14 | 172 | 2.31 | 92.2 | 93.4 |
| *A0571-ARG | NH1 | B0014-GLU | OE1 | 2.8 | 11.36 | 118 | 2.18 | 135.8 | 151.4 |
| B0011-ALA | N | *A0604-GLN | O | 2.99 | 4.47 | 129 | 2.22 | 114.7 | 120 |
| B0007-LYS | NZ | *A0604-GLN | OE1 | 3.08 | 8.25 | 155 | 2.16 | 108.4 | 107.4 |
| A0607-SER | N | B0015-GLY | OXT | 2.92 | 4.47 | 172 | 1.93 | 117.6 | 114.8 |
| A0608-LYS | NZ | B0014-GLU | O | 3.11 | 7.94 | 121 | 2.47 | 150.7 | 146.6 |
| A0616-ARG | NH1 | B0015-GLY | O | 3.01 | 11.31 | 145 | 2.1 | 128.8 | 129.8 |
| vWf - D-pep2 (SEQ ID NO: 5) | | | | | | | | | |
| B0012-CYS | N | *A0562-SER | O | 3.45 | 6.4 | 172.0 | 2.44 | 166.9 | 166.9 |
| B0013-TYR | OH | A0599-LYS | O | 2.96 | 10.0 | 142.2 | 2.15 | 109.0 | 106.9 |
| *A0599-LYS | NZ | B0008-VAL | O | 2.75 | 10.5 | 125.7 | 2.00 | 138.2 | 154.1 |
| *A0599-LYS | NZ | B0009-LEU | O | 3.31 | 8.83 | 135.5 | 2.48 | 111.0 | 123.8 |
| A0629-ARG | NE | B0004-GLU | OE1 | 2.97 | 5.74 | 155.8 | 2.02 | 94.2 | 94.6 |
| A0632-ARG | NE | B0002-GLN | O | 3.00 | 6.93 | 159.5 | 2.03 | 140.7 | 144.5 |
| *A0632-ARG | NH2 | B0002-GLN | O | 3.25 | 6.93 | 145.6 | 2.39 | 162.0 | 169.1 |
| *A0632-ARG | NH2 | B0003-ASN | OD1 | 3.28 | 6.4 | 142.3 | 2.44 | 146.3 | 156.0 |
| A0633-ASN | ND2 | B0004-GLU | O | 3.18 | 7.75 | 141.3 | 2.34 | 100.5 | 111.8 |
| vWf - D-pep3 (SEQ ID NO: 6) | | | | | | | | | |
| B0001-ARG | NE | A0560-ASP | OD1 | 2.83 | 7.62 | 138.9 | 1.97 | 115.9 | 106.2 |
| B0008-CYS | SG | A0563-HIS | NE2 | 3.38 | 5.57 | 127.6 | 2.42 | 122.8 | 105.3 |
| vWf - D-pep4 (SEQ ID NO: 7) | | | | | | | | | |
| B0005-ARG | NH2 | *A0596-GLU | OE2 | 2.77 | 11.87 | 157.6 | 1.77 | 135.1 | 135.9 |
| A0600-TYR | OH | B0015-GLU | OXT | 2.66 | 9.7 | 158 | 1.73 | 157.6 | 150.3 |
| A0629-ARG | NH2 | B0008-ASP | OD1 | 3.03 | 8.12 | 143.7 | 2.15 | 134.5 | 123.5 |
| A0637-TYR | OH | B0001-ASP | OD2 | 2.96 | 10.86 | 155.3 | 2.08 | 94.8 | 100.4 |
| B0005-ARG | NH1 | A0637-TYR | OH | 3.46 | 13.45 | 173 | 2.44 | 123.8 | 122.8 | f) Subunit: A = vWf, B = GPIb
g) Amino acid number within the subunit
h) Amino acid name
i) Atom name
j) DHA (Donor, Hydrogen, Acceptor)
*Homolog hydrogen bonds, found in the vWf-GPIb complex and in the vWf-peptide complexes.

Table 3 summarizes the characteristics of the peptide-vWf complexes and the characteristics of the inter-molecular hydrogen bonds for each of the complexes and hydrogen bonds sharing homology with those of the original vWf-GPIb complex are marked with an asterisk.

Figure 10:
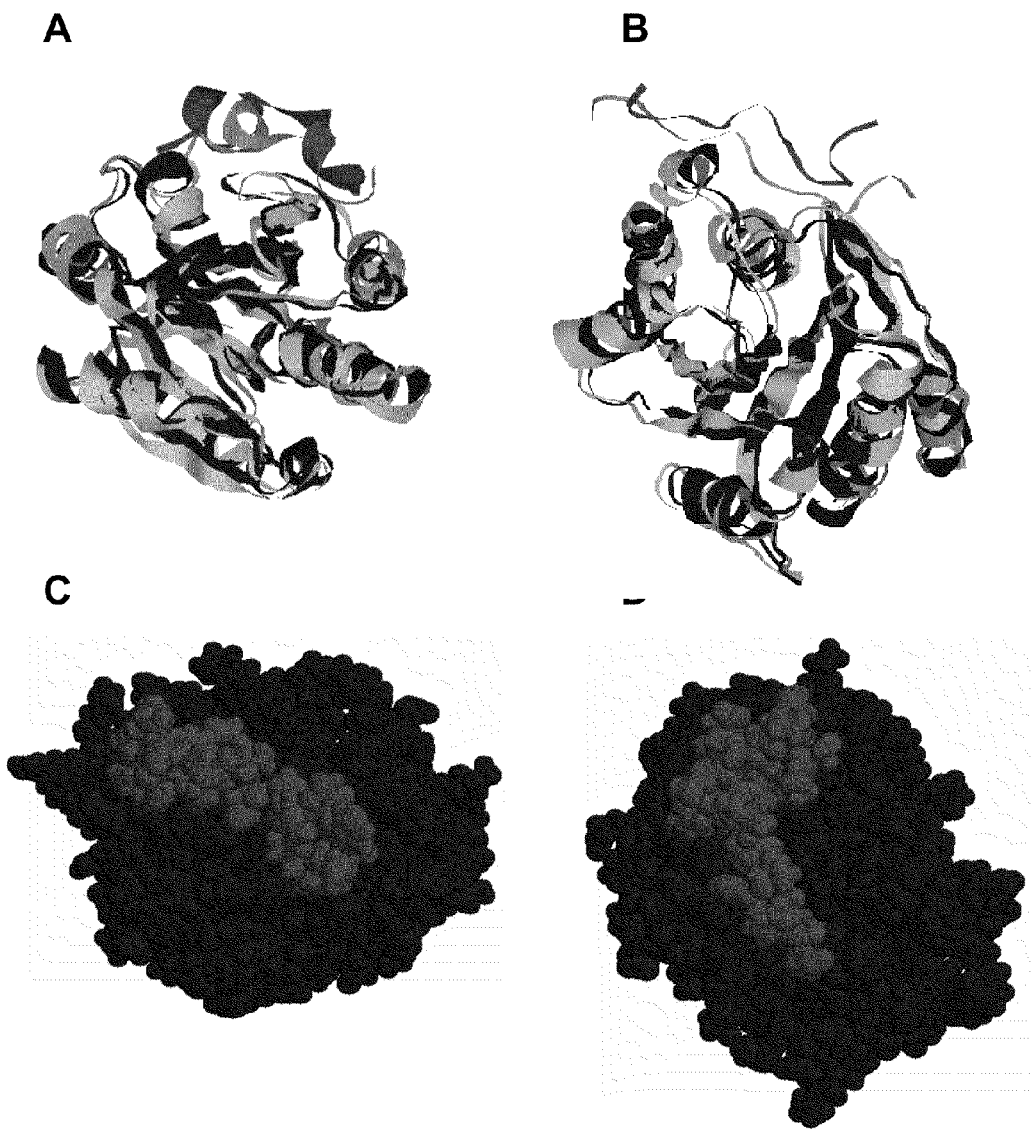
FIG. 10 shows a representation of the MIAX derived complex of vWF and each of D-pep1 (SEQ ID NO: 4) (A) and D-pep2 (SEQ ID NO: 5) (B) using molecular dynamics output; whereas complex with D-pep3 (SEQ ID NO: 6) (C) and D-pep4 (SEQ ID NO: 7) (D) are shown in a space-fill model.

FIG. 10a illustrates the position of the ligand peptide D-pep1 (SEQ ID NO:4) in the complex output as number one by MIAX, based on the scoring system as described above. The interaction can be quantified by the number of hydrogen bonds formed in the interaction interface (Table 3), where the amino acids holding the donor and acceptor atoms are listed together with the distances and angles of each hydrogen bond. Amino acids belonging to vWf are represented by chain A while amino acids of the peptide ligands are chain B in the table. Additionally, asterisks point to homolog hydrogen bonds observed in the wild type complex of vWf-GPIb. It is evident that vWf amino acids ARG571, SER562, GLN604, SER607, HIS563 and TYR565, play a critical role in the formation of this complex, although ARG571, SER607 and HIS563 are not directly involved in the vWf-GPIb interface as computed. The binding energy of the vWf-D-pep1 complex is −742.9 kcal/mol (Table 1).

FIG. 10b illustrates the position of the ligand peptide D-pep2 (SEQ ID NO:5) in the complex output as number one by MIAX. It is evident that in the case of the vWf-D-pep2 complex the amino acids of vWf ARG562, ARG599, ARG629, ARG632 and ASN633 play a critical role in the formation of the complex of which ASN633 and ARG629 were not in the computed vWf-GPIb interface. The binding energy of the vWf-D-pep2 complex is 472.33 kcal/mol (Table 1).

FIG. 10c and Table 3 summarize the characteristics of the complex obtained by docking D-pep3 (SEQ ID NO:6) with vWf. In the case of the vWf-D-pep3 complex the amino acids A560 and A563 play a critical role in the formation of the complex. Although neither of these amino acids is directly involved in the computed vWf-GPIb interface, the peptide sequence should have inhibitory activity as it binds to amino acids that are next to those involved in the interface. The binding energy of the vWf-D-pep3 complex is −805.53 kcal/mol (Table 1).

FIG. 10d and Table 3 summarize the characteristics of the complex obtained by docking D-pep4 (SEQ ID NO:7) with vWf. In the case of the vWf-D-pep4 complex that the amino acids GLU596, ARG629 and TYR637 play a critical role in the formation of the complex, and of them GLU596 is also involved in the originally computed vWf-GPIb binding interface. The binding energy of the vWf-D-pep4 complex is −1124.53 kcal/mol (Table 1).

The in vitro function of D-pep3 (SEQ ID NO:6) was confirmed by inhibition of ristocetin-mediated platelet agglutination, and quantitated by microscopy: control platelets agglutinated to ristocetin within 5 minutes but a 100-fold excess of peptide, based on plasma vWf content, prevented visible agglutination at 20 minutes. Aggregometry confirmed dose-dependent inhibition of ristocetin-initiated agglutination of washed platelets such that at 10 minutes, bovine serum albumin at 0.5 mg/mL, buffer, and 0.1 mg/mL D-pep3 (SEQ ID NO:6) gave 55%, 66% and 69% agglutination, while D-pep3 (SEQ ID NO:6) at 0.25 and 0.5 mg/mL reduced agglutination to 28% and 13% respectively. Similar patterns were observed for each of the individual blood donors tested confirming the platelet-inhibitory ability of D-pep3 (SEQ ID NO:6).

Example IV

Development of Mimotope Compounds and Enhancement of their Activity

Tandem 10-mer peptides of the vWf sequence, corresponding to overlapping sequences displaced by two amino acids including the A1 domain were synthesized as a 34×34 array on a nitrocellulose membrane. The membrane was blocked with 5% bovine serum albumin and probed with 1 mg/mL purified GPIb. Positive spots were identified by monoclonal mouse anti-human GPIb IgG (Abcam, USA) and horseradish peroxidase-coupled goat anti-mouse IgG secondary antibody (Abcam, USA). The selected amino acid sequences were threaded through the MIAX bioinformatics model and their relative contributions to free energy release upon binding to the GPIb-vWf interactive domain were calculated. As well, the binding locations of the peptides and their consequent relationship to the GPIb-vWf binding surface were confirmed. Based on binding location, solubility and traceability, the peptide SHAYIGLKDR (SEQ ID NO:8), comprising amino acids 562 to 571 of the vWf A1 domain was chosen for further development. The peptide SHAYIGLKDR (SEQ ID NO:8) remained suitable for experimental validation because of its solubility at physiological pH (net +1.1 charge at pH 7) and its traceability by spectrophotometry due to the tyrosine residue. The contribution of side-chain orientation and sequence polarity of this peptide to its activity when conjugated to HPG was tested by making its D-enantiomers and reverso-versions.

For appropriate display, a 7-mer linker sequence (SEQ ID NO:13) was defined such that together with SHAYIGLKDR (SEQ ID NO:8) the mimotopes sequences (MW=1605) became: $_L$-CGGGGGGSHAYIGLKDR (L-peptide or L-pep; SEQ ID NO:9), $_L$-CGGGGGGRDKLGIYAHS (L-retro peptide or LR-pep; SEQ ID NO:10), $_D$-CGGGGGGRDKLGIYAHS (D-peptide or D-pep; SEQ ID NO:11), $_D$-CGGGGGGRDKLGIYAHS (D-retro peptide or DR-pep; SEQ ID NO:12). These were synthesized to >93% purity as tested by HPLC. Synthesis and conjugation of the 500 kDa hyperbranched polyglycerols were conducted as follows. In a typical reaction procedure, the HPG-500 kDa polymer (100 mg) was dissolved in 3 mL dimethyl sulfoxide (DMSO, Sigma-Aldrich, Canada) and up to 20% of the n~7000 theoretical hydroxyl groups were deprotonated with 20 mg potassium hydride (30 wt % dispersion in mineral oil, Sigma-Aldrich, Canada). Divinyl sulfone, 2 µL, (DVS, corresponding to a polymer-peptide ratio of 1:100) was added and stirred at 22° C. for 12 hours. After the reaction, 2.0 mL 5.0 M HCl was added to quench the remaining KH and the reaction mixture was adjusted to neutral pH, then dialyzed through a 1000 kDa MW cut-off membrane (Spectrum Laboratories Inc., USA) to remove the potassium ions, and the VS-HPG (HPG-vinyl sulfone, bifunctionality of DVS reduced to VS after attachment to HPG) was recovered by lyophilization. For peptide coupling, 5 mg vinyl sulfone functionalized polymer was dissolved in 2 mL DMSO and stirred with an excess amount of peptide (6 mg) for 4 days at 22° C. Excess peptide was removed by dialysis through a 3000 kDa MW membrane, (Spectrum Laboratories Inc., USA) against deionized water and the conjugate was collected by lyophilization. All the conjugates were synthesized using similar amounts of divinyl sulfone and peptide. The conjugates are identified with abbreviated names: $L_{10}$ through $DR_{100}$ (Table 4), with the first letter denoting the chirality of the peptide, the second letter (if any) denoting the polarity, and the subscript denoting the conjugation ratio of peptides to HPG. For example, $LR_{10}$ represents an HPG conjugate with 10 L-retro peptides per HPG molecule.

Each peptide's binding location on GPIb was determined by MIAX. The analysis revealed a stepwise decline of association energy with GPIb as well as in the location of binding as the polarity of SHAYIGLDKR (SEQ ID NO:8) is manipulated, with the original L-version of the peptide showing the most promise, especially in term of association energy.

HPG was first derivatized with divinyl sulfone (DVS) to allow for subsequent peptide attachment. For the targeted 10:1 DVS to HPG the actual HPG-bound vinyl sulfone (VS-HPG) was calculated to be 9.75:1 by the back-titration thiol-estimation assay (Table 1). Similarly, a ratio of 99:1 was obtained for the targeted 100:1 DVS to HPG. Because excess peptide conjugation was at a level sufficient to saturate the vinyl sulfone groups, thiol-estimation was not used to quantitate the peptides on the peptide-HPG constructs. Instead, the native tyrosine residue's UV absorbance was exploited as a measure of conjugation using the molar extinction coefficient of 1260 M$^{-1}$ cm$^{-1}$ at 278 nm. 10:1 conjugates ($L_{10}$, $LR_{10}$, $D_{10}$, $DR_{10}$) were found to have approximately 9.5 peptides per HPG, and 100:1 conjugates ($L_{100}$, $LR_{100}$, $D_{100}$, $DR_{100}$) were found to have approximately 96 peptides per HPG. This confirmed the near complete or complete reaction of the VS-HPG with excess peptide.

TABLE 4

Functionalization and characterization of HPG and HPG conjugates

| Name | HPG MW | DVS per HPG | Peptides per HPG | Theoretical MW | $I_c50$ (M) | Peptide Concentration at $I_c50$ (M) |
|---|---|---|---|---|---|---|
| HPG | — | — | — | 500 kDa | No activity | 0 |
| L-pep | — | — | — | 1.605 kDa | 4.8 ± 0.6 × 10$^{-5}$*#¥ | 4.8 × 10$^{-5}$ |
| LR-pep | — | — | — | 1.605 kDa | 3.4 ± 0.3 × 10$^{-5}$*γ | 3.4 × 10$^{-5}$ |

TABLE 4-continued

Functionalization and characterization of HPG and HPG conjugates

| Name | HPG MW | DVS per HPG | Peptides per HPG | Theoretical MW | $I_c50$ (M) | Peptide Concentration at $I_c50$ (M) |
|---|---|---|---|---|---|---|
| D-pep | — | — | — | 1.605 kDa | No activity | No activity |
| DR-pep | — | — | — | 1.605 kDa | No activity | No activity |
| $L_{10}$ | 500 kDa | 9.8 ± 0.1 | 10 ± 1 | 516 kDa | $6.7 ± 0.3 × 10^{-6}$# | $6.7 × 10^{-5}$ |
| $LR_{10}$ | 500 kDa | 9.8 ± 0.1 | 10 ± 1 | 516 kDa | $4.1 ± 0.7 × 10^{-6}$ | $4.1 × 10^{-5}$ |
| $D_{10}$ | 500 kDa | 9.8 ± 0.1 | 10 ± 1 | 516 kDa | No activity | No activity |
| $DR_{10}$ | 500 kDa | 9.8 ± 0.1 | 11 ± 1 | 518 kDa | No activity | No activity |
| $L_{100}$ | 500 kDa | 98 ± 2 | 113 ± 10 | 680 kDa | $1.1 ± 0.5 × 10^{-6}$¥ | $2.1 × 10^{-4}$ |
| $LR_{100}$ | 500 kDa | 98 ± 2 | 107 ± 10 | 671 kDa | $4.9 ± 0.5 × 10^{-7}$γ | $2.2 × 10^{-5}$ |
| $D_{100}$ | 500 kDa | 98 ± 2 | 93 ± 9 | 649 kDa | No activity | No activity |
| $DR_{100}$ | 500 kDa | 98 ± 2 | 93 ± 9 | 649 kDa | No activity | No activity |

*,,, #, ¥, and γ denote p < 0.05 between the pairs.

Degranulation, downstream of GPIb-signaling, is a part of the inside-out pathway of platelet signaling during activation; it exposes CD62/P-selectin on platelet surfaces hence making CD62 quantitation a useful biomarker for platelet activation.

In order to prepare human platelets for testing, as approved by Canadian Blood Services' Ethics Board, samples of whole blood were drawn from healthy, consenting donors into 2.7-4.0 mL citrated tubes (BD, USA). Platelet rich plasma (PRP) was prepared from whole blood by centrifugation in a Beckman (CS-6R) bench-top centrifuge (r=203.57 mm, Beckman Coulter, USA) 164×g for 15 minutes. PRP from a number of unrelated donors were evaluated on an Adiva 120 Hematology Analyzer (Bayer, Canada) and standardized to a concentration of 300×10$^9$ platelets/L in HEPES buffered saline (HBS, 10 mM HEPES, 150 mM NaCl, pH 7.4).

40 μL aliquots of HBS were mixed with 5 μL PRP and 5 μL of the material to be tested: 500 kDa native HPG; free peptides; or peptide-conjugated HPG at $1.0×10^{-3}$ M to $1.0×10^{-9}$ M. After 40 minutes of incubation at ambient temperature, 5 μL 0.01 mg/mL FITC-conjugated polyclonal sheep anti-human vWf IgG (Abcam, USA) or 5 μL of 2 mg/mL PE-conjugated monoclonal mouse anti-human CD62 IgG (Beckman-Coulter, Canada) was added and incubation was continued in the dark for 30 min. Thereafter the samples were diluted and fixed with 1.0 mL 0.2% formolsaline (0.2% formaldehyde, 150 mM NaCl, pH 7.20) before analysis on a FACS Canto flow cytometer (BD, USA). Native, unconjugated HPG, free peptides, and peptide-conjugated HPG ($L_{10}$ to $DR_{100}$) incubated with resting platelets did not cause platelet activation as detected by CD62 expression (Table 5).

TABLE 5

Light microscopy, aggregometry, and flow cytometry of HPG conjugates with resting and/or activated platelets

| Assay | Microscopy of Visible Aggregates | | Aggregometry % Aggregation on Activation | Surface CD62 Expression | | vWf Binding Resting Platelets |
|---|---|---|---|---|---|---|
| | Resting Platelets | Activated Platelets | | Resting Platelets | Activated Platelets | |
| Negative Control | — | +++ | 5 ± 5 | 22 ± 2* | 30 ± 2 | 20 ± 3' |
| Positive Control | +++ | | 80 ± 5 | 90 ± 2 | 78 ± 5" | 99 ± 1 |
| HPG | — | +++ | 76 ± 5 | 22 ± 1* | 74 ± 4" | 26 ± 5' |
| L-pep | — | — | 5 ± 5 | 18 ± 1* | 72 ± 8" | 24 ± 4' |
| LR-pep | — | — | 5 ± 5 | 19 ± 2* | 70 ± 5" | 25 ± 12' |
| D-pep | — | +++ | 80 ± 5 | 18 ± 2* | 68 ± 10" | 14 ± 8' |
| DR-pep | — | +++ | 78 ± 5 | 27 ± 18* | 72 ± 3" | 28 ± 3' |
| $L_{10}$ | — | — | 5 ± 5 | 17 ± 1* | 73 ± 5" | 22 ± 5' |
| $LR_{10}$ | — | — | 5 ± 5 | 17 ± 2* | 72 ± 4" | 24 ± 2' |
| $D_{10}$ | — | +++ | 82 ± 5 | 14 ± 7* | 70 ± 6" | 24 ± 2' |
| $DR_{10}$ | — | +++ | 80 ± 5 | 19 ± 1* | 72 ± 7" | 30 ± 3' |
| $L_{100}$ | — | — | 5 ± 5 | 20 ± 3* | 71 ± 5" | 23 ± 2' |
| $LR_{100}$ | — | — | 5 ± 5 | 18 ± 1* | 73 ± 2" | 22 ± 2' |
| $D_{100}$ | — | +++ | 73 ± 5 | 18 ± 1* | 72 ± 1" | 26 ± 3' |
| $DR_{100}$ | — | +++ | 70 ± 5 | 19 ± 1* | 75 ± 3" | 18 ± 6' |

*, ", ': no significant differences were found within these groups.

The effect of native HPG, free peptides, and peptide-conjugated HPG on activated platelets using modifications of the above assay systems was also examined. Platelets were treated with either 5 μL 4.2 mg/mL ristocetin (Chrono-Log, USA) or 100 U thrombin (T6884, Sigma-Aldrich, Canada) with 5 μL GPRP fibrin inhibitor (G5779, Sigma-Aldrich, Canada) dissolved in HBS. This was done to determine whether the peptides and the peptide-conjugates can mitigate vWf and thrombin mediated platelet effects. Controls included incubation with mouse IgG-FITC/IgG-PE (Beckman-Coulter, Canada) of the same isotype, and/or omitting the conjugate. As a result, native HPG, free peptides, and peptide-conjugated HPG neither did they increase vWf binding to resting platelets (Table 5) or they could trigger platelet activation.

Peptide-conjugated HPG's inhibition of vWf binding to platelets is concentration- and substitution-dependent. The D-enantiomer-based peptides and their conjugates showed no inhibitory activity while both the L and the L-retro peptides as well as their conjugates ($L_{10}$, $L_{100}$, $L_{10}$, and $LR_{100}$) proved to be effective inhibitors (Table 4). The free L-retro peptide was a better inhibitor (p<0.05) of the GPIb-vWf interaction than the native L-peptide. This is also true for the substitution ratios (Table 4) but not the high substitution ration where the L and the L-retro were similarly active.

Figure 11:
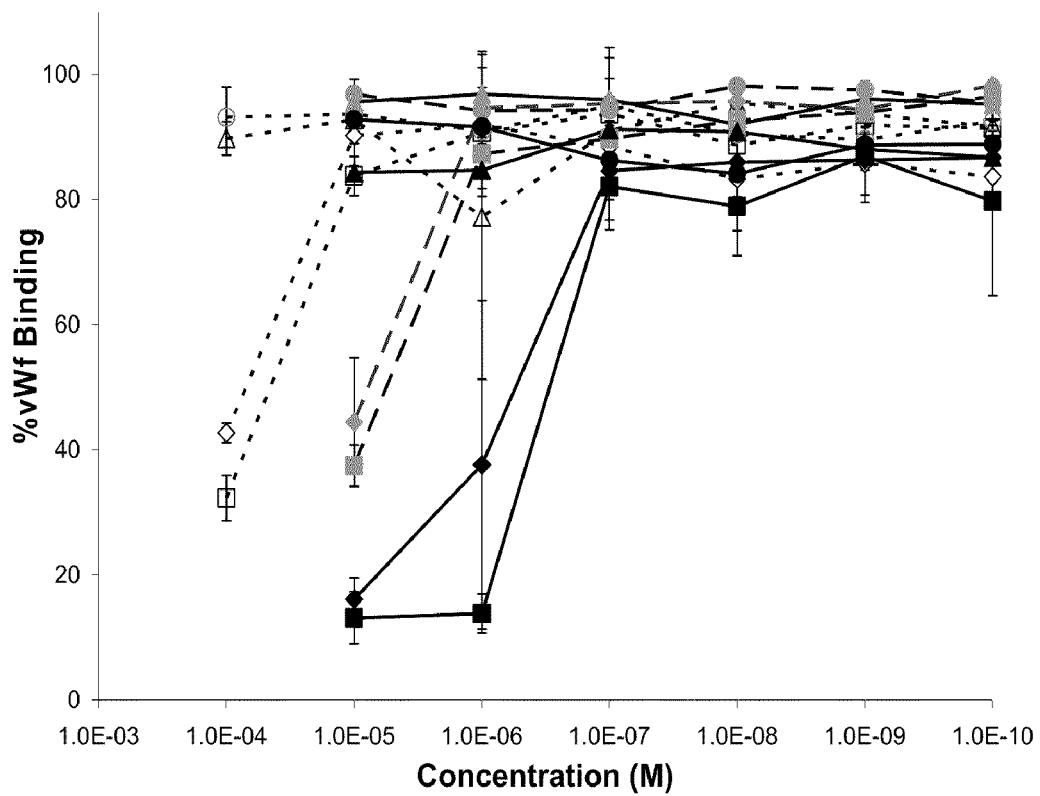
FIG. 11 shows the inhibition of platelet-vWf as a function of concentration of various peptide-conjugated hyperbranched polyglycerols (L-peptide: ◇,LR-peptide: ⊡,D-peptide: ⊙,DR-peptide: △, $L_{10}$: ◆, $LR_{10}$: ◆, $D_{10}$: ⊙, $DR_{10}$: ▲, $L_{100}$: ◆, $LR_{100}$: ■, $D_{100}$: ●, $DR_{100}$: ▲).

Based on the titration curves (FIG. 11), and the $I_C50$ values determined from them, the peptides inhibitory effectiveness was augmented by as much as two orders of magnitude by their conjugation to HPG. The specificity of SHAYGILKDR (SEQ ID NO:8) was further demonstrated by its inhibition of signaling through GPIb.

Figure 12:
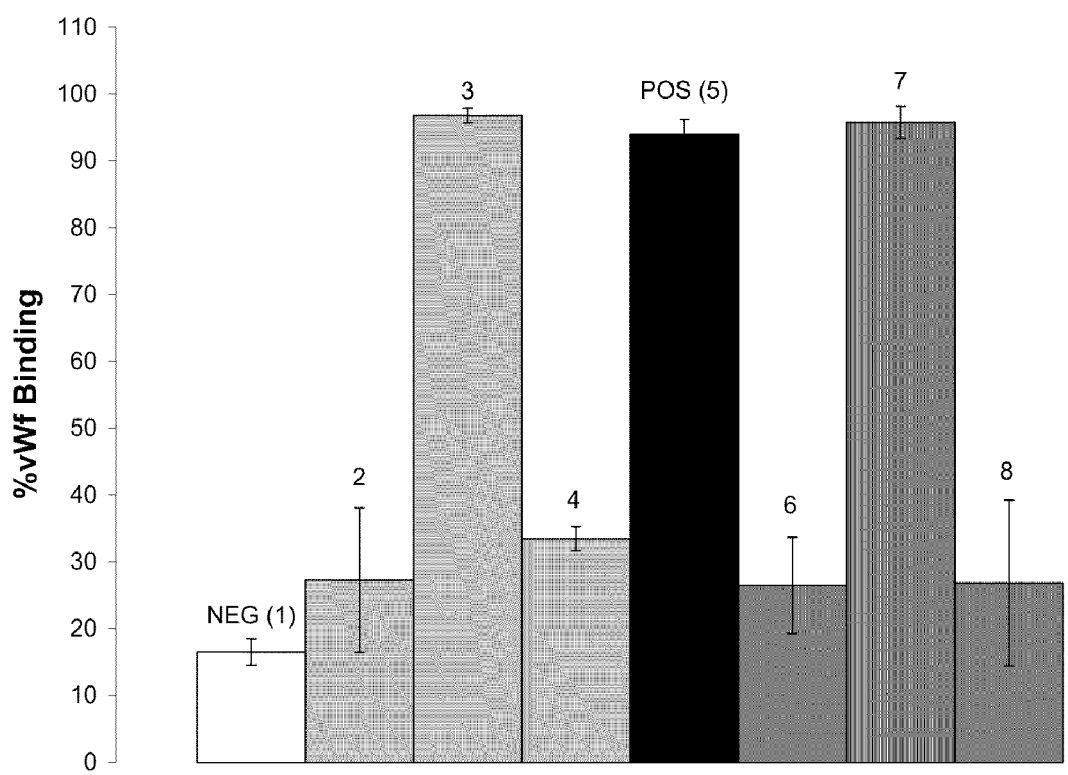
FIG. 12 shows an histogram of a trypsin proteolysis assay, wherein histogram NEG (1)=PRP platelets were checked for baseline vWf binding; histogram 2=platelets incubated with LR-peptide at $I_C50$ and activated with ristocetin; histogram 3=platelets incubated with trypsin digested LR-peptide and activated with ristocetin; histogram 4=platelets incubated with SBTI-inhibited trypsin digested LR-peptide, and activated with ristocetin; histogram POS (5)=platelets activated with ristocetin; histogram 6=platelets incubated with $LR_{100}$ conjugate at $I_C50$ and activated with ristocetin; histogram 7=platelets incubated with trypsin digested $LR_{100}$ conjugate at $I_C50$ and activated with ristocetin; and histogram 8=platelets incubated with SBTI-inhibited trypsin and activated with ristocetin.

These materials did not inhibit platelet activation by thrombin as measured by surface CD62 expression. This confirmed that the HPG-conjugates interfered solely with platelet activation mechanisms through GPIb-vWf signaling and that the inhibitory activities of the HPG-peptide conjugates are specific. The presence of the mimotope motif on the HPG is a requirement, as the loss of this function after trypsin cleavage removes the function of the conjugates (FIG. 12).

Figure 13:
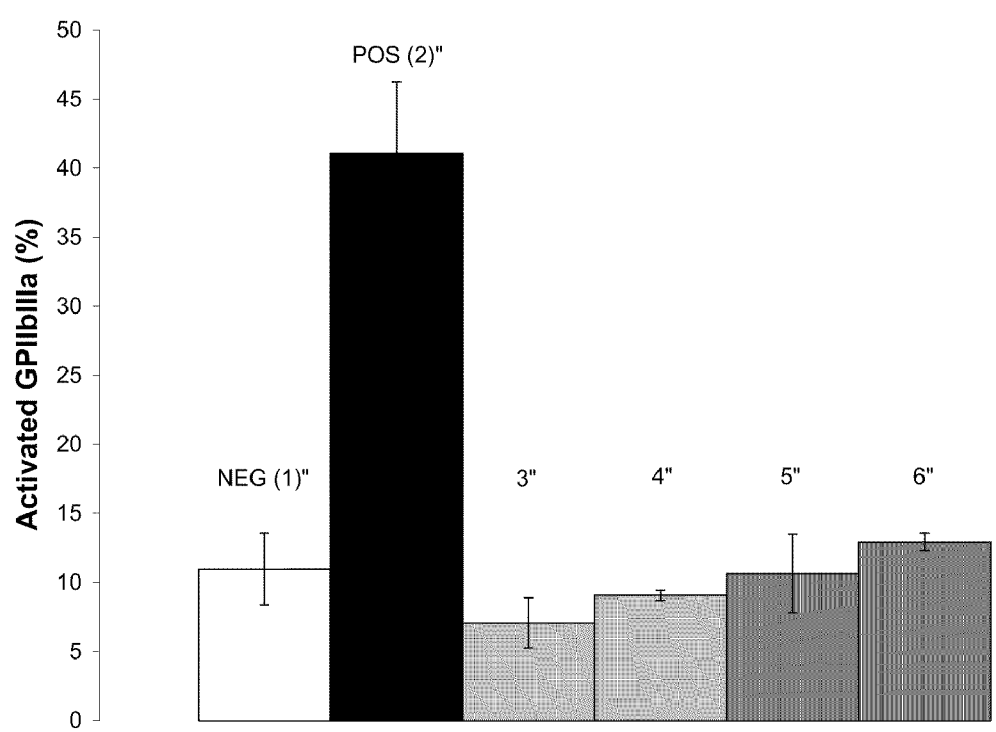
FIG. 13 shows the inhibition of GPIIbIIIa activation by $_{LR}$-SHAYIGLKDR (SEQ ID NO:8) and $LR_{100}$ conjugate, wherein the effect on GPIb signaling by the inhibitory LR-peptide and $LR_{100}$ conjugate is measured through ristocetin-mediated GPIIbIIIa activation (histogram NEG (1)=resting platelets; histogram POS (2)=ristocetin activated platelets; histogram 3=LR-peptide incubated with resting platelets; histogram 4=$LR_{100}$ incubated with resting platelets; histogram 5=LR-peptides incubated with platelets, that are then activated by ristocetin; histogram 6=$LR_{100}$ incubated with platelets, that are then activated by ristocetin).

Platelets incubated with $_L$-SHAYGILKDR and the $L_{100}$ conjugate show significantly attenuated (p<0.05) GPIIbIIIa activation upon ristocetin stimulation (FIG. 13). The inhibition of platelet agglutination by vWf was observed both by light microscopy and lumiaggregometry (Table 5). No clumping was seen when resting platelets were incubated with free peptides, native HPG, or peptide-conjugated HPG.

To show inhibition of the GPIb-vWf interaction in PRP, activation had to target the plasma component, specifically vWf, by ristocetin, rather than the consequences of platelet activators such as thrombin or ADP. Ristocetin mediated GPIb signaling was detected through GPIIbIIIa activation and flow cytometry. 5 μL resting PRP were incubated with SHAYGILKDR (SEQ ID NO:8) or $L_{100}$ at their respective $I_C50$ concentrations for 60 minutes and 5 μL 4.2 mg/mL ristocetin was used to induce platelet activation. Consequent GPIIbIIIa activation was probed via a monoclonal FITC-conjugated PAC-1 antibody to the active conformation of GPIIbIIIa (BD, Canada). Platelets did not agglutinate in the presence of ristocetin if they had been incubated with either the peptides or the peptide-conjugated HPG at their respective $I_C50$ concentration.

Accordingly, conjugation to a macromolecular carrier increased the binding of SHAYIGLKDR (SEQ ID NO:8) to GPIb and enhanced its inhibitory efficiency. The mimotope can also be designed to contain a cysteine in the linker moiety e.g. the 7-mer peptide linker: CGGGGGG (SEQ ID NO:13) implemented in this study. Conjugation to a macromolecule, whether with or without a linker, fixes the spatial orientation of the mimotope. It is demonstrated that unconjugated HPG had no contribution to vWf-binding by both resting and activated platelets (Table 5), as it seems to neither activate vWf nor bind to the GPIb-vWf interactive domain on its own. Neither did functionalized HPG and mimotope peptides promote vWf binding to resting platelets (Table 5). Furthermore, they also did not activate platelet GPIb, and did not contribute to platelet outside-in signaling as determined by surface CD62 expression (Table 5). These conjugates did not interfere with thrombin-stimulated platelet activation, and thus seem to only block GPIb-vWf signaling (Table 5). However, it is evident that these peptides and conjugates do interfere with vWf binding to platelets (FIG. 11, Table 5) in a concentration- and substitution-dependent manner. This inhibitory effect can be attributed directly to the peptide as tryptic digestion causes a loss of activity (FIG. 12). Significant differences (p<0.05) were observed between L- and L-retro peptides but not between the peptide conjugates, and no activity was observed with D-peptides. The inhibitory effects by both the peptides and the HPG-peptide conjugates on ristocetin activated platelets were confirmed by macroscopic evidence assessed by microscopy and aggregometry (Table 5). The attachment of mimotopes to HPG confers unique attributes to the resulting construct: the HPG gains specificity and function; while the mimotope gains polyvalency and consequently binding avidity. Although the $I_C50$ of the free mimotopes are not very high, it remains very clear that their conjugation to macromolecular carriers is an excellent method to increase their effectiveness.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A peptide mimotope capable of inhibiting an interaction between a platelet receptor and a platelet receptor ligand, said peptide mimotope having the amino acid sequence consisting of SEQ ID NO:6.

2. The peptide mimotope of claim 1, wherein said platelet receptor ligand is von Willebrand factor.

3. A receptor mimic capable of inhibiting an interaction between a platelet receptor and a platelet receptor ligand, said receptor mimic having the amino acid sequence consisting of SEQ ID NO:6.

4. The peptide mimotope of claim 1, said peptide mimotope being attached to a linker.

5. The peptide mimotope of claim 4, wherein said linker consist of the sequence of SEQ ID NO:13.

6. The peptide mimotope of claim 1, said peptide mimotope being conjugated to a carrier.

7. The peptide mimotope of claim 6, wherein said carrier is a liposome or an hyperbranched polyglycerol (HPG).

8. The peptide mimotope of claim 1, wherein the peptide mimotope comprises at least one D-amino acid.

9. A peptide mimotope capable of inhibiting an interaction between a platelet receptor and a platelet receptor ligand, said peptide mimotope having the amino acid sequence consisting of SEQ ID NO:6, wherein the peptide mimotope lacks amino acid sequence identity with the platelet receptor or the platelet receptor ligand.

10. The peptide mimotope of claim 1, wherein the peptide mimotope is capable of binding to one or more residues of the von Willebrand factor selected from the group consisting of H563, and D560.

11. The peptide mimotope of claim 2, wherein said platelet receptor is GPIb.

* * * * *

SEQUENCE LISTING

```
<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: von Willebrand fragment

<400> SEQUENCE: 1

Ala Cys Asp Phe Gly His Ile Lys Trp Glu Arg
 1               5                   10

<210> SEQ ID NO 2
```

```
<211> LENGTH: 11
<212> TYPE: PRT
<213> ORGANISM: Artificial Sequence
<220> FEATURE:
<223> OTHER INFORMATION: von Willebrand fragment

<400> SEQUENCE: 2

Asp Phe Gly His Ile Lys Trp Glu Arg Ala Leu
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: von Willebrand fragment

<400> SEQUENCE: 3

Gly His Ile Lys Trp Glu Arg Ala Leu Asn Asp
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Val Ser Arg Gln Asn Gly Lys Gln Tyr Trp Ala Ile Lys Glu Gly
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Trp Gln Asn Glu Gly Thr His Val Leu Ser Arg Cys Tyr Glu Cys
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Arg Ser Ala Arg Met Gln Val Cys Trp Asn Ala Phe Lys Asn Arg
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Asp Ser Cys Pro Arg Asp Trp Asp Asn Asn Phe Leu Phe Phe Glu
 1               5                  10                  15

<210> SEQ ID NO 8
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 8

Ser His Ala Tyr Ile Gly Leu Lys Asp Arg
1               5                   10

<210> SEQ ID NO 9
<211> LENGTH: 17
<212> TYPE: PRT
<213> ORGANISM: Artificial Sequence
<220> FEATURE:
<223> OTHER INFORMATION: von Willebrand fragment

<400> SEQUENCE: 9

Cys Gly Gly Gly Gly Gly Gly Ser His Ala Tyr Ile Gly Leu Lys Asp
1               5                   10                  15

Arg

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Cys Gly Gly Gly Gly Gly Gly Arg Asp Lys Leu Gly Ile Tyr Ala His
1               5                   10                  15

Ser

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Cys Gly Gly Gly Gly Gly Gly Arg Asp Lys Leu Gly Ile Tyr Ala His
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Cys Gly Gly Gly Gly Gly Gly Arg Asp Lys Leu Gly Ile Tyr Ala His
1               5                   10                  15

Ser

<210> SEQ ID NO 13
<211> LENGTH: 7
<212> TYPE: PRT
<213> ORGANISM: Artificial Sequence
<220> FEATURE:
<223> OTHER INFORMATION: Synthetic linker moiety

<400> SEQUENCE: 13

Cys Gly Gly Gly Gly Gly Gly
```

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Ala Pro Leu His Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Glu His Ile Pro Ala
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Ser Met Thr Ser Met Cys Tyr Leu Ile Gly Ala Pro Lys Tyr Lys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Lys Tyr Gln Cys Tyr Ala Pro Ala His Pro Ser Tyr Val Asn Tyr
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Phe Lys Trp Ser Trp Glu Trp Gln Gly Gln Glu Ala Tyr Tyr Asp
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Phe Arg Ile Tyr Tyr Val Tyr Thr Thr Ser Gln Gln Asp Ser Cys
1               5                   10                  15